US012780825B2

(12) United States Patent
Shen et al.

(10) Patent No.: US 12,780,825 B2
(45) **Date of Patent: *Nov. 3, 2026**

(54) SALT OF NUCLEOSIDE ANALOG, AND CRYSTAL FORM, PHARMACEUTICAL COMPOSITION AND USE THEREOF

(71) Applicants: VIGONVITA LIFE SCIENCES CO., LTD., Suzhou (CN); SHANGHAI INSTITUTE OF MATERIA MEDICA, CHINESE ACADEMY OF SCIENCES, Shanghai (CN); WUHAN INSTITUTE OF VIROLOGY, CHINESE ACADEMY OF SCIENCES, Wuhan (CN)

(72) Inventors: Jingshan Shen, Suzhou (CN); Yuanchao Xie, Suzhou (CN); Leike Zhang, Suzhou (CN); Gengfu Xiao, Suzhou (CN); Zhen Wang, Suzhou (CN); Hualiang Jiang, Suzhou (CN); Huaqiang Xu, Suzhou (CN); Tianwen Hu, Suzhou (CN); Guanghui Tian, Suzhou (CN)

(73) Assignees: VIGONVITA LIFE SCIENCES CO., LTD., Jiangsu (CN); SHANGHAI INSTITUT OF MATERIA MEDICA, CHINESE ACADEMY OF SCIENCES, Shanghai (CN); WUHAN INSTITUTE OF VIROLOGY, CHINESE ACADAMY, Wuhan (CN)

( * ) Notice: Subject to any disclaimer, the term of this patent is extended or adjusted under 35 U.S.C. 154(b) by 600 days.

This patent is subject to a terminal disclaimer.

(21) Appl. No.: 18/033,673

(22) PCT Filed: Oct. 21, 2021

(86) PCT No.: PCT/CN2021/125379

§ 371 (c)(1),
(2) Date: Apr. 25, 2023

(87) PCT Pub. No.: WO2022/089302

PCT Pub. Date: May 5, 2022

(65) Prior Publication Data

US 2023/0312584 A1 Oct. 5, 2023

(30) Foreign Application Priority Data

Oct. 26, 2020 (CN) ......................... 202011156037.5
Dec. 18, 2020 (CN) ......................... 202011505962.4

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................... C07D 487/04
See application file for complete search history.

(56) References Cited

U.S. PATENT DOCUMENTS 11,919,923 B2 * 3/2024 Xie ....................... C07F 9/6561
12,351,599 B2 * 7/2025 Xie ....................... C07F 9/6561

FOREIGN PATENT DOCUMENTS

| | | | |
|---|---|---|---|
| CN | 110330540 | A | 10/2019 |
| CN | 111961057 | A | 11/2020 |
| CN | 112778310 | A | 5/2021 |
| EP | 4141007 | A1 | 3/2023 |
| IN | 202227061975 | A | 9/2022 |
| JP | 2017-534614 | A | 11/2017 |
| JP | 2018-531227 | A | 10/2018 |
| WO | 2018/204198 | A1 | 11/2018 |
| WO | 2021/022690 | A1 | 2/2021 |

OTHER PUBLICATIONS

Casares, Journal of Pharmacy and Pharmacology, 67, 2015, pp. 812-822 (Year: 2017).*
Casares, Journal of Pharmacy and Pharmacology, 67, 2015, pp. 812-822 (Year: 2015).*
Acharya, Dosage Form Design Considerations, vol. I, 2018, pp. 435-472 (Year: 2018).*

(Continued)

*Primary Examiner* — John S Kenyon
*Assistant Examiner* — Phillip Matthew Rzeczycki
(74) *Attorney, Agent, or Firm* — Oliff PLC

(57) ABSTRACT

A salt of nucleoside analog, and crystal form, pharmaceutical composition and use thereof. The salt of nucleoside analog has a structure shown in formula I, wherein X is hydrogen or deuterium; Y is an acid, n is 0.5 to 2, or n is 1. When X is hydrogen or deuterium, Y is hydrogen bromide, and n is 1, the salt of the nucleoside analog exists in the form of a crystal with crystal form I or crystal form A or exists in an amorphous form.

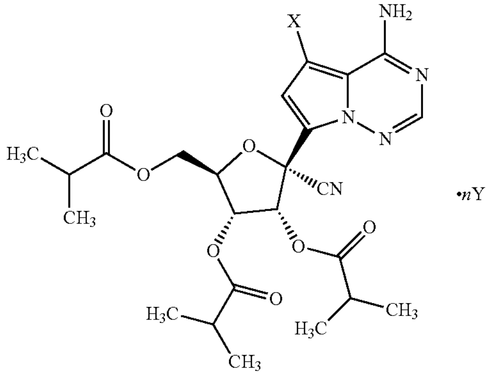

16 Claims, 7 Drawing Sheets

(56) References Cited

OTHER PUBLICATIONS

Dec. 22, 2021 International Search Report issued in International Patent Application No. PCT/CN2021/125379.
Dec. 22, 2021 Written Opinion issued in International Patent Application No. PCT/CN2021/125379.
Xie et al., "Design and development of an oral remdesivir derivative VV116 against SARS-CoV-2", Cell Research, vol. 31, Sep. 28, 2021, pp. 1212-1214.
Wei et al., "Potency and pharmacokinetics of GS-441524 derivatives against SARS-CoV-2", Bioorganic & Medicinal Chemistry, vol. 46, No. 11, Aug. 2021, pp. 1-12.
Mackman et al., "Prodrugs of a 1'-CN-4-Aza-7,9-dideazaadenosine C-Nucleoside Leading to the Discovery of Remdesivir (GS-5734) as a Potent Inhibitor of Respiratory Syncytial Virus with Efficacy in the African Green Monkey Model of RSV", Journal of Medicinal Chemistry, vol. 64, No. 8, Apr. 9, 2021, pp. 5001-5017.
Johnson et al., "Structural basis of nucleoside and nucleoside drug selectivity by concentrative nucleoside transporters", eLife, 2014, pp. 1-19.
Yin et al., "Structural Basis for Repurpose and Design of Nucleoside Drugs for Treating COVID-19", BioRxiv, Nov. 2, 2020, pp. 1-49.

* cited by examiner

SALT OF NUCLEOSIDE ANALOG, AND CRYSTAL FORM, PHARMACEUTICAL COMPOSITION AND USE THEREOF

CROSS-REFERENCE TO RELATED APPLICATION

The present disclosure claims the priority to and the benefit of Chinese Patent Application No. 202011156037.5, filed on Oct. 26, 2020, with the title of "Salt of Nucleoside Analog, and Crystal Form, Pharmaceutical Composition and Use Thereof", and Chinese Patent Application No. 202011505962.4, filed on Dec. 18, 2020, with the title of "Salt of Nucleoside Analog, and Crystal Form, Pharmaceutical Composition and Use Thereof", the entire contents of which are incorporated herein by reference.

TECHNICAL FIELD

The present disclosure pertains to the technical field of medicine, and specifically relates to an acid addition salt of a nucleoside analog, a salt-based crystal, a pharmaceutical composition and a medical use.

BACKGROUND

Viral infectious diseases pose a serious threat to human life and health. At present, there are many types of viruses that have been found to cause human diseases. With the expansion of the scope of human social activities and the strengthening of the globalization trend, novel or re-emerging viruses continue to appear around the world, such as the SARS-CoV in 2003, the H1N1 influenza virus in 2009, the H7N9 avian influenza virus in 2013, the MERS-CoV in 2012, the Ebola virus in 2014, and the dengue virus and Zika virus that have become more prevalent in recent years. Most of these viruses have the characteristics of fast transmission, strong infectivity and high morbidity, which pose severe challenges to the world's medical and health system.

Severe acute respiratory syndrome coronavirus 2 (SARS-CoV-2) is a novel coronavirus with approximately 79% genome-wide similarity to the SARS-CoV in 2003. Since its discovery, this virus has spread rapidly around the world.

Because viruses have strong capability of proliferation, and are prone to mutation during the replication process, many viral infections can hardly be prevented by vaccination, and antiviral drugs are one of the important means to fight against viruses. As an organism, a virus uses DNA or RNA as its genetic material, and its replication requires a large amount of nucleoside triphosphates or deoxynucleoside triphosphates. The use of nucleoside analogs to interfere with the replication of viral genetic material is an important strategy for the discovery of antiviral drugs.

In summary, there is an urgent need in this field to develop nucleoside analogs with stable physical properties and good druggability for the treatment of related diseases caused by viral infections.

SUMMARY

Technical Problem

The object of the present disclosure is to provide an acid addition salt of a nucleoside analog with stable physical properties and good druggability, a salt-based crystal obtained based on the acid addition salt, a pharmaceutical composition comprising the acid addition salt or the salt-based crystal thereof, and to provide a corresponding preparation method and pharmaceutical use.

Solutions

In a first aspect, the present disclosure provides a compound of formula I,

I

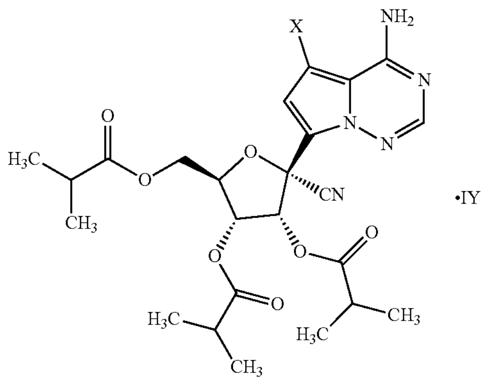

wherein X is hydrogen or deuterium; Y is maleic acid, succinic acid, citric acid, tartaric acid, fumaric acid, formic acid, acetic acid, propionic acid, malonic acid, oxalic acid, benzoic acid, phthalic acid, methanesulfonic acid, ethanesulfonic acid, benzenesulfonic acid, toluenesulfonic acid, naphthalenesulfonic acid, 1,5-naphthalenedisulfonic acid, camphoric acid, camphorsulfonic acid, salicylic acid, acetylsalicylic acid, aspartic acid, glutamic acid, lactic acid, gluconic acid, ascorbic acid, gallic acid, mandelic acid, malic acid, sorbic acid, trifluoroacetic acid, taurine, homotaurine, 2-hydroxyethanesulfonic acid, cinnamic acid, mucic acid, hydrogen chloride, hydrogen bromide, hydrogen iodide, sulfuric acid, nitric acid, phosphoric acid, perchloric acid or a combination thereof, preferably hydrogen bromide, hydrogen chloride, nitric acid, methanesulfonic acid, maleic acid or a combination thereof, more preferably hydrogen bromide; n is 0.5 to 2, preferably 1.

Preferably, the compound of formula I is a compound of formula I-1:

I-1

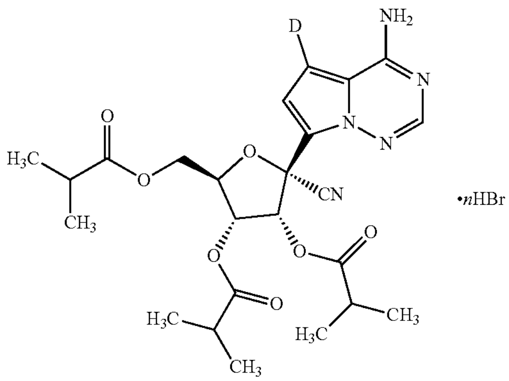

wherein n is 0.5 to 2, preferably 1.

More preferably, the compound of formula I or formula I-1 is a compound of formula I-1'.

I-1'

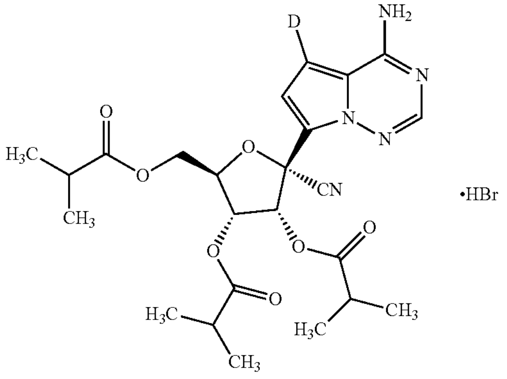

Preferably, the compound of formula I-1' is a crystal in the form of a crystal form A, the crystal form A has at least one of the following characteristics: 1) an XRPD pattern of the crystal form A at least having characteristic peaks at 3 positions, preferably 5 positions and more preferably 7 positions among the following 2θ values of 5.35°±0.2°, 8.11°±0.2°, 8.46°±0.2°, 15.70°±0.2°, 18.08°±10.2°, 21.09°±0.2° and 21.91°±0.2°; 2) a DSC spectrum of the crystal form A having an absorption peak at 204±5° C.; 3) after being placed under conditions of 25° C. and RH80% for 24 hours, the crystal form A showing an increase in moisture content of 1% or less, preferably 0.2% or less, and more preferably 0.1% or less; and 4) at 37° C., the crystal form A having a solubility in deionized water of 0.1 mg/mL or more, preferably 0.2 mg/mL or more, and more preferably 0.3 mg/mL.

More preferably, the XRPD pattern of the crystal form A further at least has characteristic peaks at 3 positions, preferably 5 positions and more preferably 8 positions among the following 2θ values of 16.02°±0.2°, 16.88°±0.2°, 17.22°±0.2°, 17.76°±0.2°, 20.55°±0.2°, 23.25°±0.2°, 23.89°±0.2° and 26.14°±0.2°; most preferably, the XRPD pattern of the crystal form A is shown in FIG. 2.

More preferably, the DSC spectrum of the crystal form A is shown in FIG. 1.

Alternatively, the compound of formula I-1' is preferably an amorphous substance.

More preferably, an XRPD pattern of the amorphous substance is shown in FIG. 6.

Preferably, the compound of formula I is a compound of formula I-2:

I-2

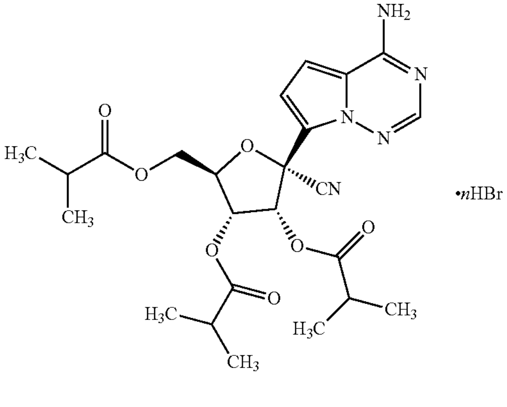

wherein n is 0.5 to 2, preferably 1.

More preferably, the compound of formula I or formula I-2 is a compound of formula I-2'.

I-2'

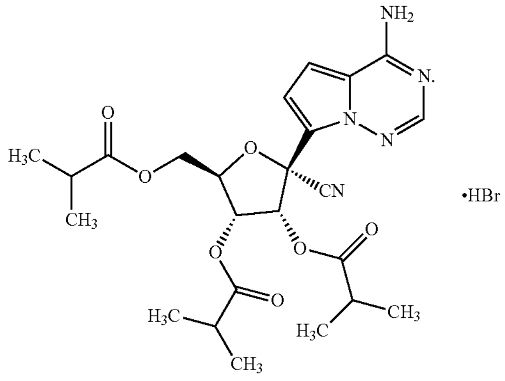

Preferably, the compound of formula I-2' is a crystal in the form of a crystal form I, the crystal form I has at least one of the following characteristics: 1) an XRPD pattern of the crystal form I at least having characteristic peaks at 3 positions, preferably 5 positions, and more preferably 6 positions among the following 2θ values of 5.36°±0.2°, 8.13°±0.2°, 8.48°±0.2°, 18.16°±0.2°, 20.95°±0.2° and 21.95°±0.2°; 2) a DSC spectrum of the crystal form I having an absorption peak at 200±5° C.; 3) after being placed under conditions of 25° C. and RH80% for 24 hours, the crystal form I showing an increase in moisture content of 1% or less, preferably 0.2% or less, and more preferably 0.1% or less; and 4) at 37° C., the crystal form I having a solubility in deionized water of 0.1 mg/mL or more, preferably 0.2 mg/mL or more, and more preferably 0.3 mg/mL.

More preferably, the XRPD pattern of the crystal form I further at least has characteristic peaks at 3 positions, preferably 5 positions, and more preferably 7 positions among the following 2θ values of 15.71°±0.2°, 16.07°±0.2°, 16.90°±0.2°, 17.26°±0.2°, 20.55°±0.2°, 23.27°±0.2° and 26.08°±0.2°; most preferably, the XRPD pattern of the crystal form I is shown in FIG. 4.

More preferably, the DSC spectrum of the crystal form I is shown in FIG. 3.

Alternatively, the compound of formula I-2' is preferably an amorphous substance.

More preferably, an XRPD pattern of the amorphous substance is shown in FIG. 7.

In a second aspect, the present disclosure provides a preparation method of a compound shown in formula I, formula I-1, formula I-1', formula I-2 or formula I-2', comprising the following steps of:

1) dissolving a compound of formula II in a solvent A to obtain a solution A, and mixing the solution A with an acid or a solution B obtained by dissolving the acid in a solvent B under an ice bath condition to obtain a mixed solution;

II

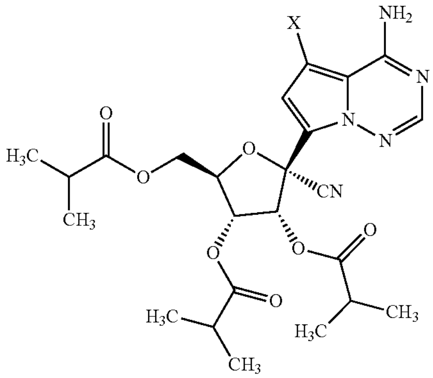

wherein X is hydrogen or deuterium;

the acid is maleic acid, succinic acid, citric acid, tartaric acid, fumaric acid, formic acid, acetic acid, propionic acid, malonic acid, oxalic acid, benzoic acid, phthalic acid, methanesulfonic acid, ethanesulfonic acid, benzenesulfonic acid, toluenesulfonic acid, naphthalenesulfonic acid, 1,5-naphthalenedisulfonic acid, camphoric acid, camphorsulfonic acid, salicylic acid, acetylsalicylic acid, aspartic acid, glutamic acid, lactic acid, gluconic acid, ascorbic acid, gallic acid, mandelic acid, malic acid, sorbic acid, trifluoroacetic acid, taurine, homotaurine, 2-hydroxyethanesulfonic acid, cinnamic acid, mucic acid, hydrogen chloride, hydrogen bromide, hydrogen iodide, sulfuric acid, nitric acid, phosphoric acid, perchloric acid or a combination thereof, preferably hydrogen bromide, hydrogen chloride, nitric acid, methanesulfonic acid, maleic acid or a combination thereof, more preferably hydrogen bromide; and 2) stirring and concentrating the mixed solution at room temperature to obtain a target product.

Preferably, in step 1) of the preparation method, a dosage ratio of the compound of formula II to the solvent A is 1 g:2 to 20 mL, preferably 1 g:5 to 10 mL; in the solution B, a content of the acid is 40 wt % to 50 wt %; a molar ratio of the compound of formula II to the acid is 1:0.9 to 1; in step 2) of the preparation method, the stirring lasts for 0.5 to 5 hours, preferably 0.5 to 1 hour.

Preferably, the preparation method further comprises a step 3) of mixing the product in step 2) with a solvent C, stirring at room temperature and/or under a heating condition to precipitate a solid as the target product.

More preferably, in step 3) of the preparation method, a dosage ratio of the compound of formula II to the solvent C is 1 g:2 to 20 mL, preferably 1 g:5 to 15 mL; the heating condition is heating at a temperature ranging from 35 to 60° C., preferably from 50 to 60° C.; and the stirring lasts for 0.5 to 5 hours, preferably 0.5 to 2 hours.

Preferably, in the preparation method, the solvent A, the solvent B and the solvent C are each independently selected from the group consisting of water, hydrocarbon, alcohol, ether, ketone, ester, nitrile and a homogeneous mixture thereof; the hydrocarbon is selected from the group consisting of n-pentane, n-hexane, n-heptane, petroleum ether, dichloromethane, chloroform, carbon tetrachloride, 1,2-dichloroethane, benzene, toluene, xylene, chlorobenzene and dichlorobenzene; the alcohol is selected from the group consisting of methanol, ethanol, n-propanol, isopropanol, n-butanol, ethylene glycol and propylene glycol; the ether is selected from the group consisting of ethyl ether, n-propyl ether, isopropyl ether, methyl tert-butyl ether, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, dioxane, dimethoxyethane and diglyme; the ketone is selected from the group consisting of acetone, butanone and diethyl ketone; the ester is selected from the group consisting of methyl formate, ethyl formate, propyl formate, butyl formate, methyl acetate, ethyl acetate, propyl acetate and butyl acetate; the nitrile is selected from the group consisting of acetonitrile and propionitrile; and the solvent A is miscible with the solvent B.

More preferably, in step 1) of the preparation method, the solvent A is acetonitrile; a dosage ratio of the compound of formula II and the acetonitrile is 1 g:2 to 20 mL, preferably 1 g:5 to 10 mL; the acid is hydrogen bromide, the solvent B is water, the solution B is hydrobromic acid, and a content of hydrogen bromide in the hydrobromic acid is 40 wt % to 50 wt %; a molar ratio of the compound of formula II to the hydrogen bromide is 1:0.9 to 1; in step 2) of the preparation method, the stirring lasts for 0.5 to 5 hours, preferably 0.5 to 1 hour; in step 3) of the preparation method, the solvent C is methyl tert-butyl ether; a dosage ratio of the compound of formula II and the methyl tert-butyl ether is 1 g:2 to 20 mL, preferably 1 g:5 to 15 mL; the heating condition is heating at a temperature ranging from 35 to 60° C., preferably from 50 to 60° C.; and the stirring lasts for 0.5 to 5 hours, preferably 0.5 to 2 hours.

In a third aspect, the present disclosure provides a pharmaceutical composition comprising a compound of formula I, formula I-1, formula I-1', formula I-2 or formula I-2'; and an optional pharmaceutically acceptable excipient.

Preferably, the pharmaceutical composition is an oral formulation or a non-oral formulation. More preferably, the oral formulation is selected from the group consisting of tablet, capsule, granule, powder and syrup; the non-oral formulation is selected from the group consisting of injection, powder for injection, spray and suppository.

In a fourth aspect, the present disclosure provides a compound of formula I, formula I-1, formula I-1', formula I-2 or formula I-2' or a pharmaceutical composition comprising the compound for use in the treatment and/or alleviation of a disease caused by a virus. Preferably, the virus is SARS-CoV-2.

In a fifth aspect, the present disclosure provides use of a compound of formula I, formula I-1, formula I-1', formula I-2 or formula I-2' or a pharmaceutical composition comprising the compound in the preparation of a medicament for the treatment and/or alleviation of a disease caused by a virus. Preferably, the virus is SARS-CoV-2.

In a sixth aspect, the present disclosure provides a method for treating and/or alleviating a disease caused by a virus, comprising a step of administering a therapeutically and/or palliatively effective amount of a compound of formula I, formula I-1, formula I-1', formula I-2 or formula I-2' or a pharmaceutical composition comprising the compound to a subject in need thereof. Preferably, the virus is SARS-CoV-2.

In a seventh aspect, the present disclosure provides a method for inhibiting virus replication, comprising a step of contacting the virus with an inhibitory effective amount of a compound of formula I, formula I-1, formula I-1', formula I-2 or formula I-2' or a pharmaceutical composition comprising the compound. Preferably, the virus is SARS-CoV-2.

Advantageous Effects

After extensive and in-depth research, the present disclosure conducts the synthesis, isolation, and related study on the physicochemical properties of acid addition salts of nucleoside analogs with antiviral activity (especially anti-SARS-CoV-2 activity) and crystals thereof, and it is unexpectedly found that acid addition salts (e.g., hydrobromide, hydrochloride and maleate of Compound Z, as well as hydrobromide and maleate of Compound W) and their corresponding crystalline forms (e.g., crystal form A and crystal form I) with advantages of good appearance as solid material, high stability, good solubility, and low hygroscopicity, can be used in the preparation of medicaments for the treatment and/or alleviation of related diseases caused by viruses (especially SARS-CoV-2). Moreover, besides being easy to perform and reproduce, the preparation method in the present disclosure also has advantages of high purity, constant composition, and easy storage of the product, and others.

DETAILED DESCRIPTION

Definition of Terms

Nucleoside Analog

Figure 1:
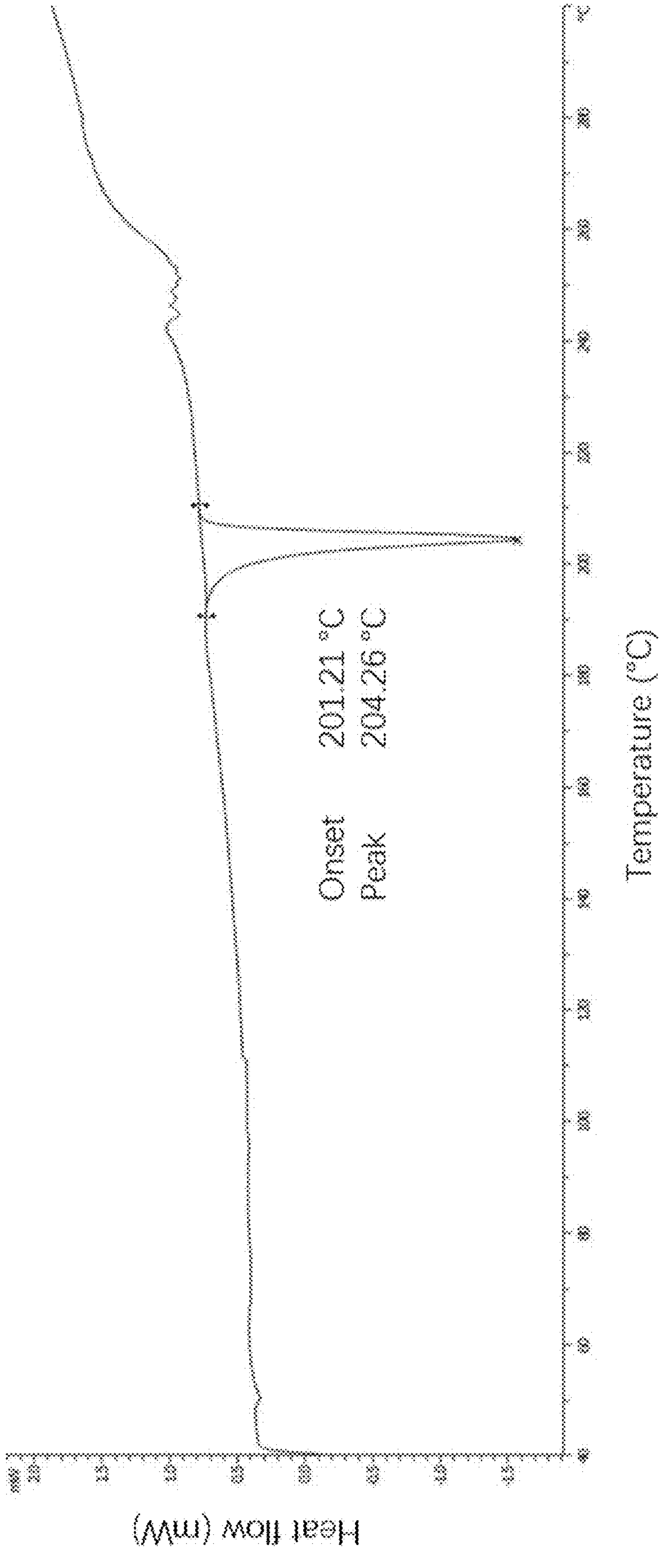
FIG. 1 shows the DSC spectrum of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrobromide (hydrobromide of Compound Z) in the form of a crystal with crystal form A.

Nucleoside analog is the most important class of antiviral drugs. For a long time, it has played an important role in the clinical treatment of viral diseases. Nucleoside drug can be converted into corresponding triphosphate in vivo. Especially during the stage of virus replication, nucleoside triphosphate can "disguised" as substrate and be incorporated into the DNA or RNA chain of the virus, thereby inhibiting the replication of genetic material and exerting an antiviral effect.

Compound Z and Compound W

Compound Z

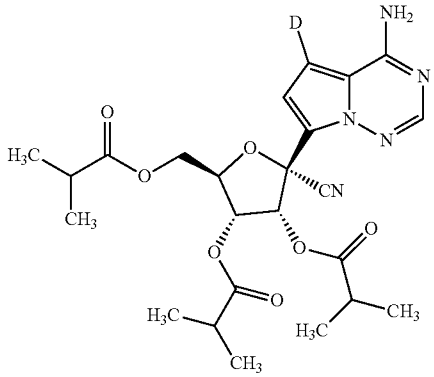

Compound W

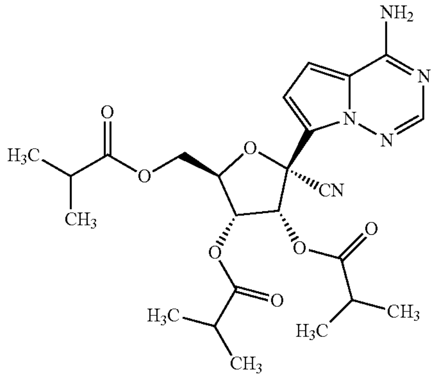

Compound Z and compound W are described in Chinese Patent Application No. CN 202010313870.X. According to experimental tests, these compounds have significant anti-SARS-CoV-2 activity and a good inhibitory effect on a variety of other RNA viruses. However, Compound Z and Compound W, as free bases, are viscous oils at room temperature, leading to poor druggability. Therefore, it is particularly important to seek for the solid form of Compound Z and Compound W; moreover, when used as a pharmaceutical preparation, Compound Z and Compound W have the problem of poor water solubility, which has a certain impact on the preparation process.

Salt and Solvate

Unless otherwise specified, the "salt" described in the present disclosure includes both pharmaceutically acceptable salt (or pharmaceutical salt) and pharmaceutically unacceptable salt. Pharmaceutically unacceptable salt is not preferably administered to patients but useful in providing pharmaceutical intermediates and bulk pharmaceutical forms.

Unless otherwise specified, the "pharmaceutically acceptable salt" or "pharmaceutically acceptable acid addition salt" described in the present disclosure refers to acid addition salt prepared using pharmaceutically acceptable acid, including (but not limited to) organic acid salt and inorganic acid salt; the acid used for salification is preferably hydrobromic acid, hydrochloric acid, sulfuric acid, nitric acid, methanesulfonic acid or maleic acid, more preferably hydrobromic acid or maleic acid, and most preferably hydrobromic acid.

When the acid addition salt of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) (Compound Z) or (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) (Compound W) of the present disclosure is placed in the air or recrystallized, moisture will be absorbed, thereby producing a hydrate in the form of adsorbed water, and the acid addition salt containing moisture is also included within the scope of the present disclosure.

In addition, the present disclosure further covers a solvate formed by the acid addition salt of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) (Compound Z) or (2R,3R,4R,5R)-2-(4-aminopyrrolo[2,1-f][1,2,4]triazin-7-yl)-2-cyano-5-(isobutyryloxymethyl) tetrahydrofuran-3,4-diyl bis(2-methylpropanoate) (Compound W) with a solvent, and there is no particular limitation as long as it is the solvent used in the preparation of the salt and/or crystal. Specifically, for example, a hydrate, an alcohol solvate, an acetone solvate, an ester solvate, an etherate, a toluene solvate, and the like may be used, and a hydrate or an alcohol solvate is preferable.

Pharmaceutical Composition

Unless otherwise specified, the "pharmaceutical composition" described in the present disclosure comprises at least one compound of the present disclosure, and optional pharmaceutically acceptable excipients. Preferably, the pharmaceutical composition in the present disclosure comprises at least one acid addition salt formed from a free base selected from the group consisting of Compound Z and Compound W and an acid selected from the group consisting of hydrogen bromide, hydrogen chloride, sulfuric acid, nitric acid, methanesulfonic acid and maleic acid, and optional pharmaceutically acceptable excipients. More preferably, the pharmaceutical composition in the present disclosure comprises a hydrobromide of Compound Z with crystal form A and/or a hydrobromide of Compound W with crystal form I, and optional pharmaceutically acceptable excipients.

Unless otherwise specified, the "excipient" described in the present disclosure includes (but not limited to) a diluent, a binder, a lubricant, a disintegrant, a colorant, a flavoring agent, a deodorant, an emulsifier, a surfactant, a cosolvent, a suspending agent, an isotonicity agent, a buffer, a preservative, an antioxidant, a stabilizer, an absorption enhancer, and the like commonly used in the pharmaceutical field. The above-mentioned excipients can also be used in appropriate combinations as required.

When used as a therapeutic or preventive drug for viral infectious diseases, the acid addition salt (i.e., the compound of formula I) of Compound Z or Compound W of the present disclosure can be used alone or in admixture with suitable pharmaceutically acceptable excipients, in the form of an oral formulation such as tablet, capsule, granule, powder or syrup, or in the form of a non-oral formulation such as injection, powder for injection, spray or suppository. All these preparation forms can be prepared by conventional preparation methods in the art.

In the oral pharmaceutical composition, the hydrobromide of Compound W or Compound Z of the present disclosure is formulated in admixture with at least one pharmaceutically acceptable excipient, and each unit dose contains 10 to 2000 mg of active pharmaceutical ingredient (API). For example, when the oral pharmaceutical composition is a tablet, the API and at least one pharmaceutical excipient (e.g., starch, lactose, magnesium stearate, etc.) are mixed and compressed into tablet form, and the plain tablet can be further coated with sugar coating or other suitable substances, or be treated so that the tablet exhibits a sustained-release or controlled-release effect. As another example, when the oral pharmaceutical composition is a capsule, the API is mixed with at least one diluent (e.g., starch) and optionally pelletized, granulated, and the resulting mixture is filled into a capsule shell.

Medicinal Use

The dosage of medication varies with symptoms, age, etc. Taking an adult as an example, the medicament can be administered 1 to 7 times every 1 to 7 days according to symptoms, at a dosage of about 0.01 to 1000 mg, without limitation to the administration route.

The compound of the present disclosure can be used to treat and/or alleviate diseases caused by viral infections, or to inhibit viral replication. These viruses include (but not limited to) coronavirus, influenza virus, respiratory syncytial virus, virus in the flaviviridae family, virus in the filoviridae family and porcine epidemic diarrhea virus (PEDV), preferably coronavirus, and more preferably SARS-CoV-2. Therefore, the compound of the present disclosure can be used to prepare corresponding antiviral drugs.

The present disclosure will be further elaborated below in conjunction with specific examples. It should be understood that these examples are only used to illustrate the present disclosure and not to limit the scope of the present disclosure. In the following examples, experimental methods that do not specify specific conditions were usually carried out in accordance with conventional conditions, such as conditions described in Sambrook et al., Molecular Cloning: A Laboratory Manual (New York: Cold Spring Harbor Laboratory Press, 1989), or as suggested by the manufacturers. Unless otherwise specified, percentages and parts in the present disclosure are all by weight.

Reagents and Consumables Instructions

In the examples of the present disclosure, reagents such as acetonitrile involved in the preparation method were all analytically pure, provided by Sinopharm Chemical Reagent Co., Ltd., and all reagents used had not been specifically treated unless otherwise specified. (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) (Compound Z) and (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) (Compound W) were prepared with reference to the examples in patent application CN202010313870X, the purity was greater than 98%, and the deuterium content was greater than 98%. Triethylamine and phosphoric acid involved in the HPLC experiment were chromatographically pure, provided by Sinopharm Chemical Reagent Co., Ltd. NMR spectra were measured on Brucker 500 Hz and Brucker 600 Hz NMR spectrometers.

General Test Methods

1. X-ray Powder Diffraction (XRPD) Test Method

Instrument: Bruker D8 advance X-ray polycrystalline diffractometer; target: Cu-Kα (40 kV, 40 mA); sample-to-detector distance: 30 cm; scan type: two-axis linkage; scan step width: 0.02°; scan range: 3° to 40°; scan step: 0.1 s.

In general, the diffraction angle (2θ value) in XRPD may have an error within a range of ±0.2°, so the numerical values related to the diffraction angle in the present disclosure should be understood to also include values in the range of about ±0.2°. Therefore, the present disclosure not only covers crystal forms that are completely consistent with the characteristic signal peaks in the specific XRPD pattern, but also covers crystal forms that have an error of about ±0.2° with the characteristic signal peaks in the specific XRPD pattern.

2. DSC Test Method

Instrument: METTLER TOLEDO Differential Scanning calorimeter; temperature range: 50-260° C.; scan rate: 20° C./min; nitrogen flow rate: 50 mL/min.

3. Hygroscopicity Test Method

An appropriate amount of a test product is taken and spread in a glass-stoppered weighing bottle that has been placed in an artificial climate box (temperature is 25° C.±1° C., relative humidity is 80%±2%) for 24 hours. The weighing bottle is opened, put together with the stopper in the artificial climate box (the temperature is 25° C.±1° C., the relative humidity is 80%±2%) for 24 hours, and then taken out. The moisture content of the test product before and after being placed in the artificial climate box is measured, and the hygroscopicity is measured by comparing the change in moisture content.

4. Stability Test Method

The test product is placed in suitable clean containers, and then placed under conditions of high temperature (80° C.), high humidity (25° C., relative humidity 92.5%), and light (light intensity 4500±500 1× and 90 μw/$cm^2$), respectively, for 7 days, and samples are taken on the 7th day and tested according to the stability inspection items.

5. Solubility Test Method

About 10 mg of the test product is taken and put in a 1.5 mL sample tube, to which 1 mL of deionized water is added, and then the sample tube is placed in a constant temperature mixer and shaken at 37° C. for 30 minutes; after shaking, the sample tube is placed in a centrifuge to undergo centrifugation for 2 minutes. Then, 500 μL of the supernatant is taken and diluted with acetonitrile to an appropriate concentration, which is used as a test sample solution for HPLC analysis. The solubility of the test product in water (37° C.) is calculated according to an external standard method.

Example 1: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrobromide

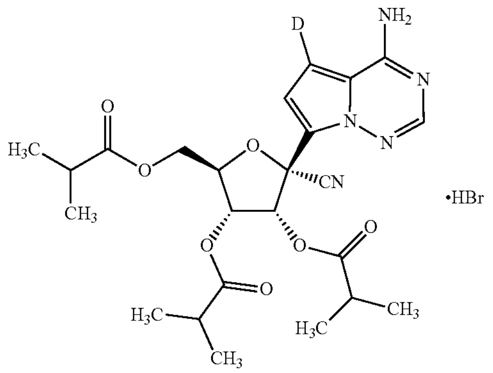

(2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) (Compound Z, the same below) (12 g, 23.90 mmol) was dissolved in acetonitrile (100 mL), to which 40% hydrobromic acid (4.37 g, 21.6 mmol) was added dropwise in an ice bath. After the addition was completed, the mixture was returned to room temperature and stirred. After 30 minutes, the reaction solution was concentrated, methyl tert-butyl ether (150 mL) was added, and the mixture was stirred for 30 minutes. Solid was precipitated. The temperature was raised to 55° C., and stirring was continued for 2 hours, then the mixture was cooled to room temperature, filtered after standing, and dried to obtain the title compound (10.8 g, yield 78%, HPLC purity 99.2%) as a white solid.

$^1$H-NMR (600 MHz, $CDCl_3$): δ 13.05 (s, 1H), 9.73 (s, 1H), 9.46 (s, 1H), 8.00 (s, 1H), 7.04 (s, 1H), 6.02 (d, J=5.8 Hz, 1H), 5.41 (dd, J=5.8, 4.0 Hz, 1H), 4.65 (q, J=4.0 Hz, 1H), 4.40-4.33 (m, 2H), 2.71-2.60 (m, 2H), 2.58-2.52 (m, 1H), 1.26-1.22 (m, 6H), 1.21-1.18 (m, 6H), 1.17-1.13 (m, 6H).

$^{13}$C-NMR (150 MHz, DMSO-$d_6$): δ 176.01, 175.35, 174.59, 150.65, 139.98, 125.81, 115.79, 115.43, 112.21, 82.22, 75.64, 73.33, 70.72, 62.99, 33.67, 33.62, 33.56, 19.11, 19.02, 18.92, 18.87, 18.85, 18.70.

MS: m/z 503.1 [ M+1]$^+$.

The result of differential scanning calorimetry (DSC) showed that the obtained solid showed an endothermic peak with an onset at 201.21° C. and a peak at 204.26° C., as shown in FIG. 1.

Figure 2:
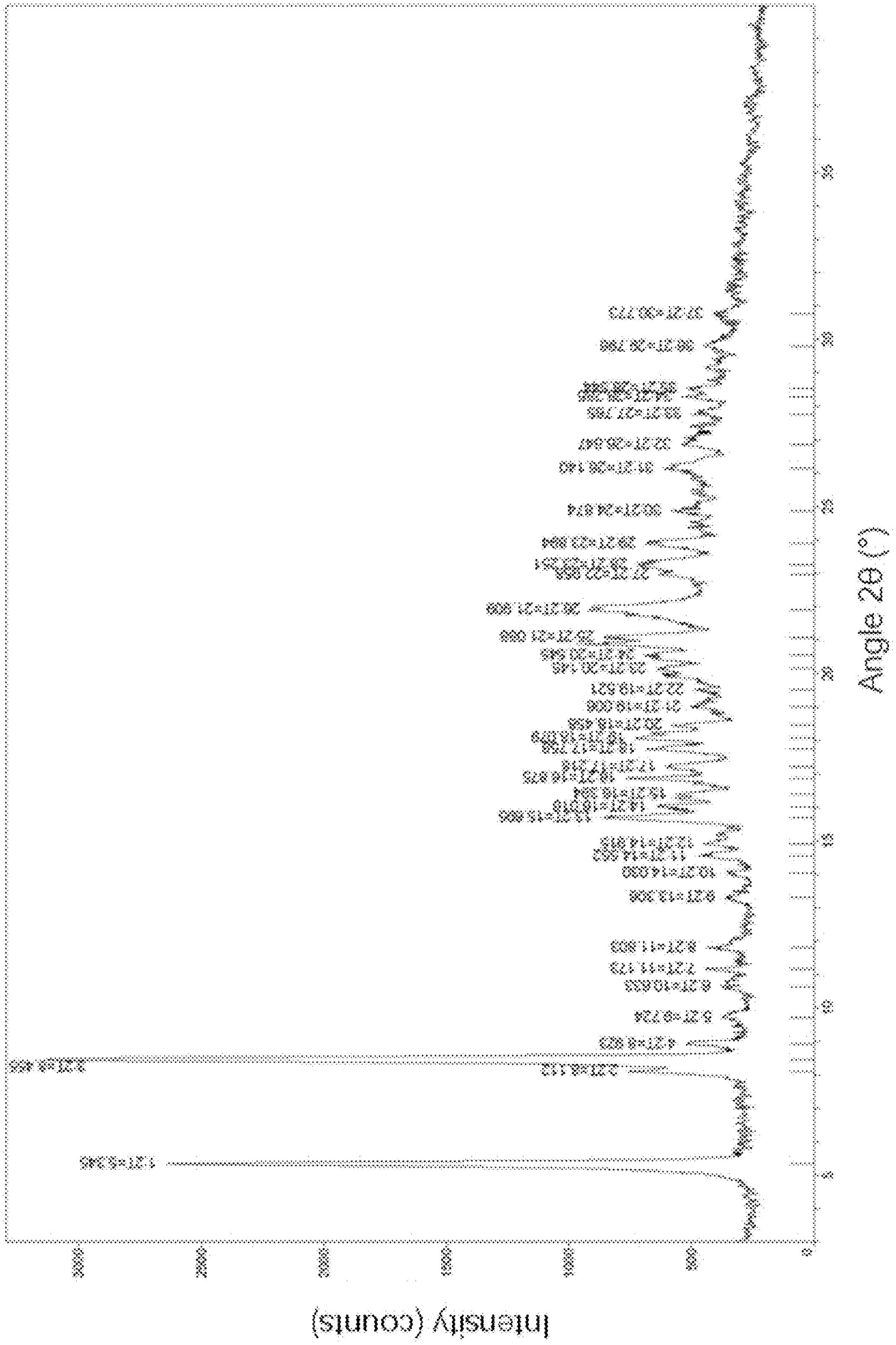
FIG. 2 shows the XRPD pattern of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrobromide (hydrobromide of Compound Z) in the form of a crystal with crystal form A.

The result of X-ray powder diffraction (XRPD) showed that the obtained solid was in crystalline form, corresponding to crystal form A, as shown in Table 1 and FIG. 2.

TABLE 1

XRPD data for the hydrobromide of Compound Z with crystal form A

| Peak number | Diffraction angle (2θ, °) | Intensity ($I/I_0$, %) |
|---|---|---|
| 1 | 5.345 | 75 |
| 2 | 8.112 | 27 |
| 3 | 8.455 | 100 |
| 4 | 8.923 | 2 |

TABLE 1-continued

XRPD data for the hydrobromide of Compound Z with crystal form A

| Peak number | Diffraction angle (2θ, °) | Intensity ($I/I_0$, %) |
|---|---|---|
| 5 | 9.724 | 3 |
| 6 | 10.633 | 4 |
| 7 | 11.173 | 5 |
| 8 | 11.803 | 5 |
| 9 | 13.306 | 3 |
| 10 | 14.030 | 3 |
| 11 | 14.552 | 4 |
| 12 | 14.915 | 5 |
| 13 | 15.695 | 20 |
| 14 | 16.016 | 15 |
| 15 | 16.394 | 8 |
| 16 | 16.875 | 12 |
| 17 | 17.218 | 10 |
| 18 | 17.758 | 11 |
| 19 | 18.079 | 26 |
| 20 | 18.458 | 7 |
| 21 | 19.006 | 4 |
| 22 | 19.521 | 3 |
| 23 | 20.145 | 7 |
| 24 | 20.545 | 13 |
| 25 | 21.088 | 19 |
| 26 | 21.909 | 27 |
| 27 | 22.958 | 13 |
| 28 | 23.251 | 16 |
| 29 | 23.894 | 8 |
| 30 | 24.874 | 6 |
| 31 | 26.140 | 14 |
| 32 | 26.847 | 8 |
| 33 | 27.765 | 1 |
| 34 | 28.285 | 5 |
| 35 | 28.544 | 8 |
| 36 | 29.796 | 2 |
| 37 | 30.773 | 3 |

Figure 6:
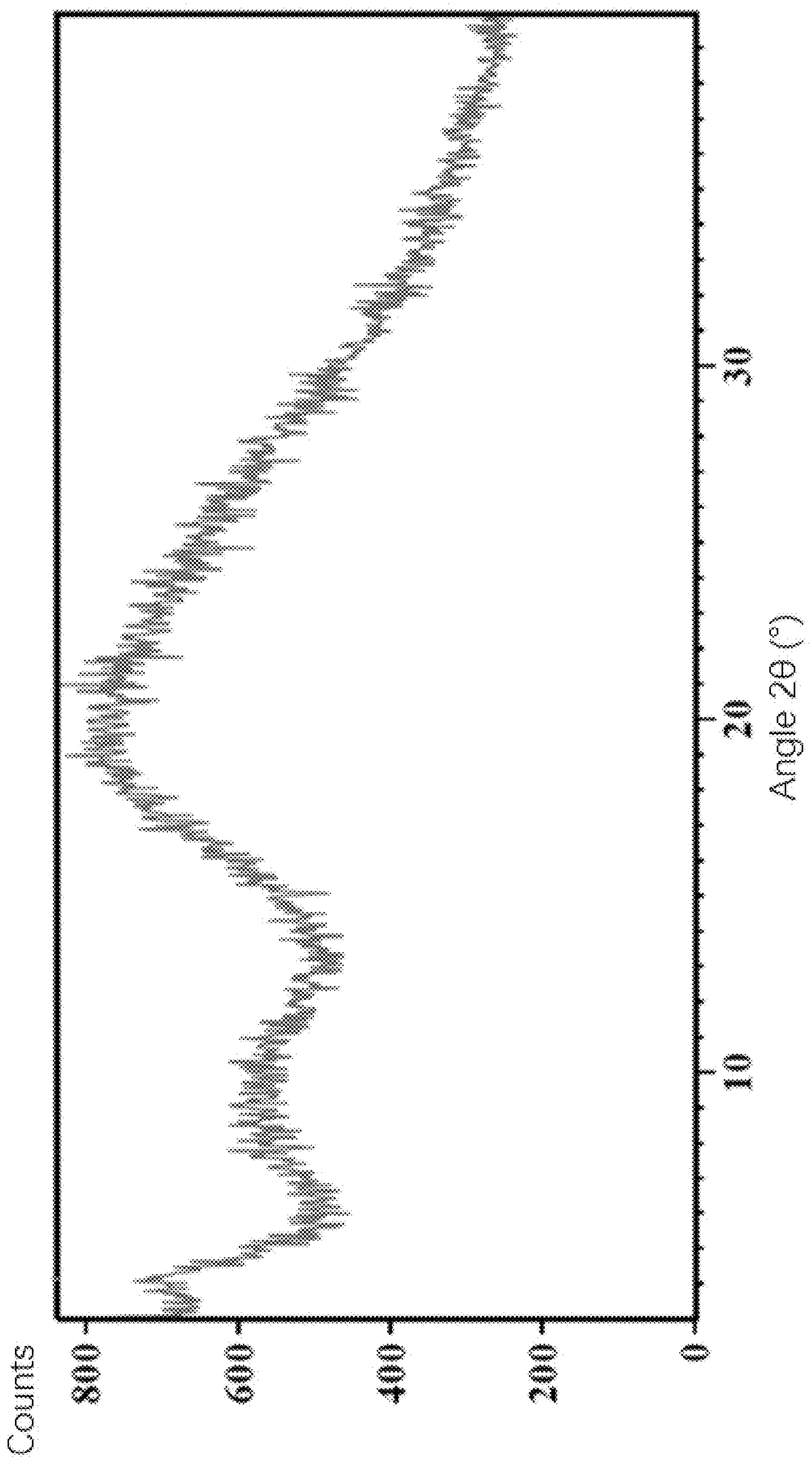
FIG. 6 shows the XRPD pattern of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrobromide (hydrobromide of Compound Z) in amorphous form.

The solid powder (2.5 g) of the hydrobromide (I-1') of Compound Z with crystal form A was added into ethanol (10 mL), and stirred at room temperature. After the solid was completely dissolved, the solution was concentrated to remove the solvent, and drained by an oil pump to obtain a powdered solid (2.5 g). The results of X-ray powder diffraction (XRPD) showed that the obtained solid was amorphous, as shown in FIG. 6.

Example 2: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrochloride

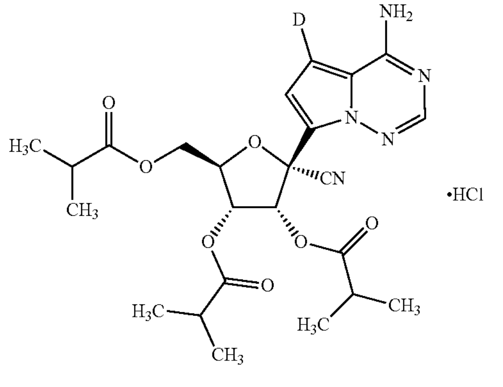 [SMILES: [2H]c1cc([C@]2(C#N)O[C@H](COC(=O)C(C)C)[C@@H](OC(=O)C(C)C)[C@H]2OC(=O)C(C)C)n2ncnc(N)c12 ; Br]

Compound Z (210 mg, 0.42 mmol) was dissolved in acetonitrile (8 mL), to which 36% concentrated hydrochloric acid (50 mg, 0.49 mmol) was added dropwise in an ice bath. After the addition, the mixture was returned to room temperature and stirred. 20 minutes later, the reaction solution was concentrated, a mixed solution of isopropyl acetate and n-heptane (V/V=1:1, 12 mL) was added, and a cotton wool-like solid was precipitated. The solution was heated to 60° C., stirred for 30 minutes, slowly cooled to 0° C., and further stirred for 30 minutes. A gelatinous system was generated and then filtered with difficulty, and the filtration residue was dried to obtain the title compound (120 mg, yield 53%, HPLC purity 98.9%) as a white solid.

$^1$H-NMR (500 MHz, $CDCl_3$): δ 13.60 (s, 1H), 10.48 (s, 1H), 9.69 (s, 1H), 8.05 (s, 1H), 7.03 (s, 1H), 6.05 (d, J=5.8 Hz, 1H), 5.48-5.40 (m, 1H), 4.66 (q, J=3.9 Hz, 1H), 4.47-4.31 (m, 2H), 2.75-2.50 (m, 3H), 1.29-1.24 (m, 6H), 1.24-1.12 (m, 12H).

MS: m/z 503.1 [ M+1]$^+$.

Example 3: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) nitrate

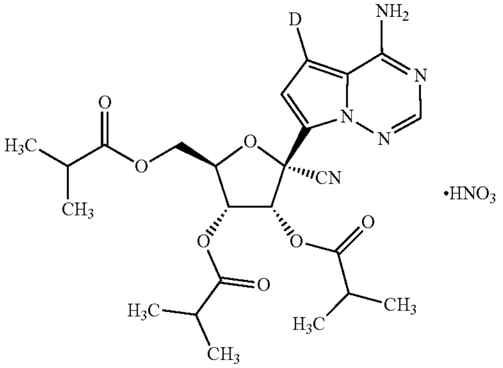

Compound Z (53 mg, 0.1 mmol) was dissolved in acetonitrile (0.5 mL), to which 65% nitric acid (10 mg, 0.1 mmol) was added in an ice bath. After stirring for 30 minutes, the reaction solution was concentrated, to which isopropyl acetate (4 mL) was added. A white solid was precipitated. After stirring for 1 hour, the residue obtained by filtration was dried to obtain the title compound (45 mg, yield 80%, HPLC purity 99.0%) as a white solid.

$^1$H-NMR (500 MHz, $CDCl_3$): δ 9.79 (s, 1H), 9.58 (s, 1H), 7.99 (s, 1H), 7.06 (s, 1H), 6.07 (d, J=5.8 Hz, 1H), 5.49-5.41 (m, 1H), 4.68 (q, J=3.9 Hz, 1H), 4.46-4.34 (m, 2H), 2.75-2.63 (m, 2H), 2.62-2.53 (m, 1H), 1.30-1.26 (m, 6H), 1.24-1.21 (m, 6H), 1.19 (t, J=7.2 Hz, 6H).

MS: m/z 503.1 [M+1]$^+$.

Example 4: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) mesylate

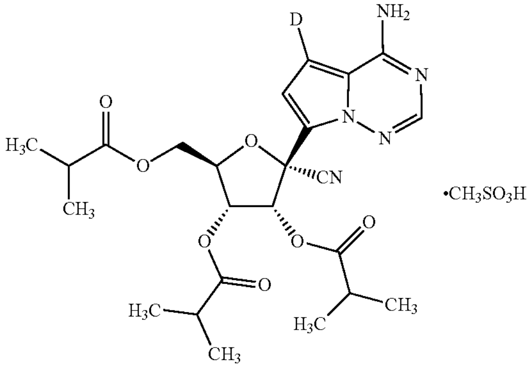

Compound Z (8.07 g, 16.07 mmol) was dissolved in isopropyl acetate (80 mL), to which methanesulfonic acid (1.54 g, 16.07 mmol) was added dropwise in an ice bath. After the addition, the mixture was stirred at room temperature for 30 minutes, and then n-heptane (80 mL) was added. There was a large amount of cotton wool-like solid precipitated. The mixture was heated to 60° C., stirred for 30 minutes, then cooled to 0° C., and further stirred for 30 minutes. A large amount of solid was precipitated, and the residue obtained by filtration was dried to obtain the title compound (8.0 g, yield 83%, HPLC purity 99.1%) as a white solid.

$^1$H-NMR (600 MHz, $CDCl_3$): δ 13.60 (s, 1H), 9.98 (s, 1H), 9.91 (s, 1H), 7.76 (s, 1H), 6.97 (s, 1H), 6.01 (d, J=5.8 Hz, 1H), 5.45-5.38 (m, 1H), 4.64 (q, J=3.9 Hz, 1H), 4.40-4.30 (m, 2H), 2.94 (s, 3H), 2.71-2.64 (m, 1H), 2.64-2.58 (m, 1H), 2.57-2.50 (m, 1H), 1.27-1.22 (m, 6H), 1.21-1.11 (m, 12H).

MS: m/z 503.1 $[M+1]^+$.

Example 5: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) maleate

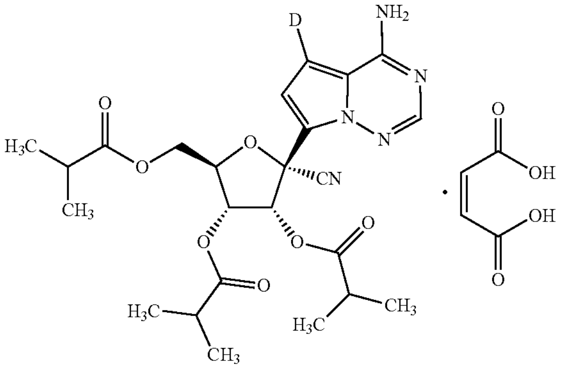

Compound Z (2.85 g, 5.67 mmol) was dissolved in absolute ethanol (20 mL), to which maleic acid (0.66 g, 5.67 mmol) was added, and the mixture was heated to reflux. After 30 minutes, the reaction solution was cooled to room temperature, and n-heptane (40 mL) was added. There was a large amount of cotton wool-like solid precipitated. The mixture was heated to 45° C., stirred for 1.5 hours, cooled to 0° C., and further stirred for 30 minutes. The residue obtained by filtration was dried to obtain the title compound (2.5 g, yield 71%, HPLC purity 98.9%) as a white solid.

$^1$H-NMR (600 MHz, DMSO-$d_6$): δ 8.11 (s, 1H), 8.01 (s, 1H), 7.94 (s, 1H), 6.76 (s, 1H), 6.26 (s, 2H), 6.07 (d, J=5.7 Hz, 1H), 5.44 (dd, J=5.7, 3.7 Hz, 1H), 4.63 (q, J=3.7 Hz, 1H), 4.33 (dd, J=12.4, 3.3 Hz, 1H), 4.28 (dd, J=12.4, 4.1 Hz, 1H), 2.67-2.56 (m, 2H), 2.49-2.45 (m, 1H), 1.17 (d, J=7.0 Hz, 3H), 1.15 (d, J=7.0 Hz, 3H), 1.12-1.09 (m, 6H), 1.05 (d, J=7.0 Hz, 3H), 1.02 (d, J=7.0 Hz, 3H).

MS: m/z 503.1 $[M+1]^+$.

Example 6: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hemisulfate

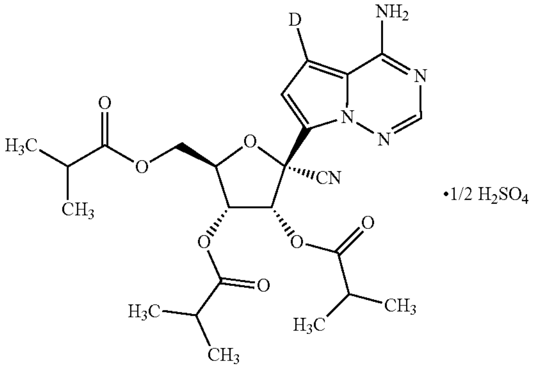 [SMILES: [2H]c1cc([C@]2(C#N)O[C@H](COC(=O)C(C)C)[C@@H](OC(=O)C(C)C)[C@H]2OC(=O)C(C)C)n2ncnc(N)c12 ; "·1/2 H2SO4"]

Referring to the methods of Examples 1-5, for the salt formation of Compound Z with 0.5 equivalent of sulfuric acid, no solid was precipitated in the system.

Example 7: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) sulfate

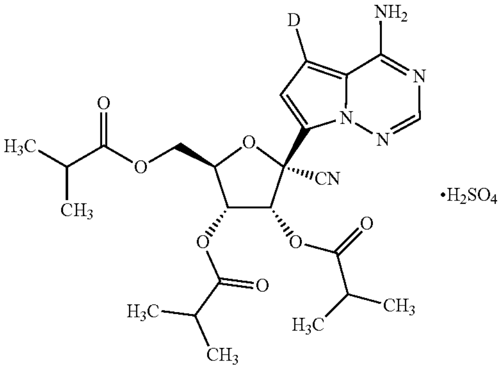

Referring to the methods of Examples 1-5, for the salt formation of Compound Z with 1.0 equivalent of sulfuric acid, no solid was precipitated in the system.

Example 8: Preparation of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) phosphate

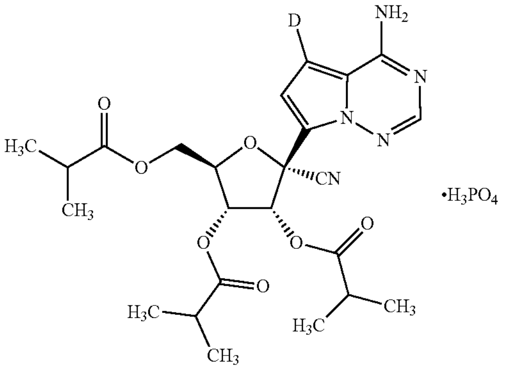

Referring to the methods of Examples 1-5, for the salt formation of Compound Z with 1.0 equivalent of phosphoric acid, no solid was precipitated in the system.

Example 9: Preparation of (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) hydrobromide

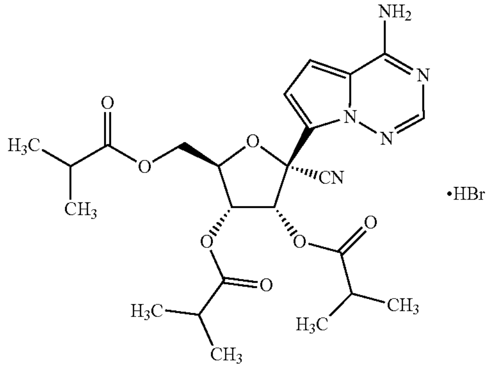 [SMILES: CC(C)C(=O)OC[C@H]1O[C@@](C#N)(c2ccc3c(N)ncnn23)[C@H](OC(=O)C(C)C)[C@@H]1OC(=O)C(C)C ; Br]

(2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) (Compound W, the same below) (550 mg, 1.1 mmol) was dissolved in acetonitrile (100 mL), to which 40% hydrobromic acid (202 mg, 1.0 mmol) was added dropwise in an ice bath. After the addition, the mixture was returned to room temperature and stirred. After 30 minutes, the reaction solution was concentrated, to which methyl tert-butyl ether (8 mL) was added. The mixture was stirred at room temperature for 30 minutes, and a solid was precipitated. The mixture was heated to 55° C., and further stirred for 2 hours, cooled to room temperature, filtered after standing, and dried to obtain the title compound (0.5 g, yield 78%, HPLC purity 99.1%) as a white solid.

$^{1}H$-NMR (500 MHz, $CDCl_3$): δ 12.92 (br, 1H), 9.98 (s, 1H), 9.46 (s, 1H), 8.09 (s, 1H), 7.97 (d, J=4.8 Hz, 1H), 7.03 (d, J=4.8 Hz, 1H), 6.03 (d, J=5.9 Hz, 1H), 5.43 (dd, J=5.9, 4.1 Hz, 1H), 4.64 (q, J=4.1 Hz, 1H), 4.43-4.33 (m, 2H), 2.73-2.52 (m, 3H), 1.27-1.22 (m, 6H), 1.22-1.18 (m, 6H), 1.18-1.14 (m, 6H).

$^{13}C$-NMR (150 MHz, DMSO-$d_6$): δ 176.01, 175.36, 174.60, 151.03, 140.54, 125.55, 115.97, 115.47, 112.22, 107.79, 82.19, 75.68, 73.29, 70.72, 62.99, 33.67, 33.62, 33.56, 19.11, 19.02, 18.92, 18.87, 18.85, 18.70.

MS: m/z 502.1 $[M+1]^+$.

Figure 3:
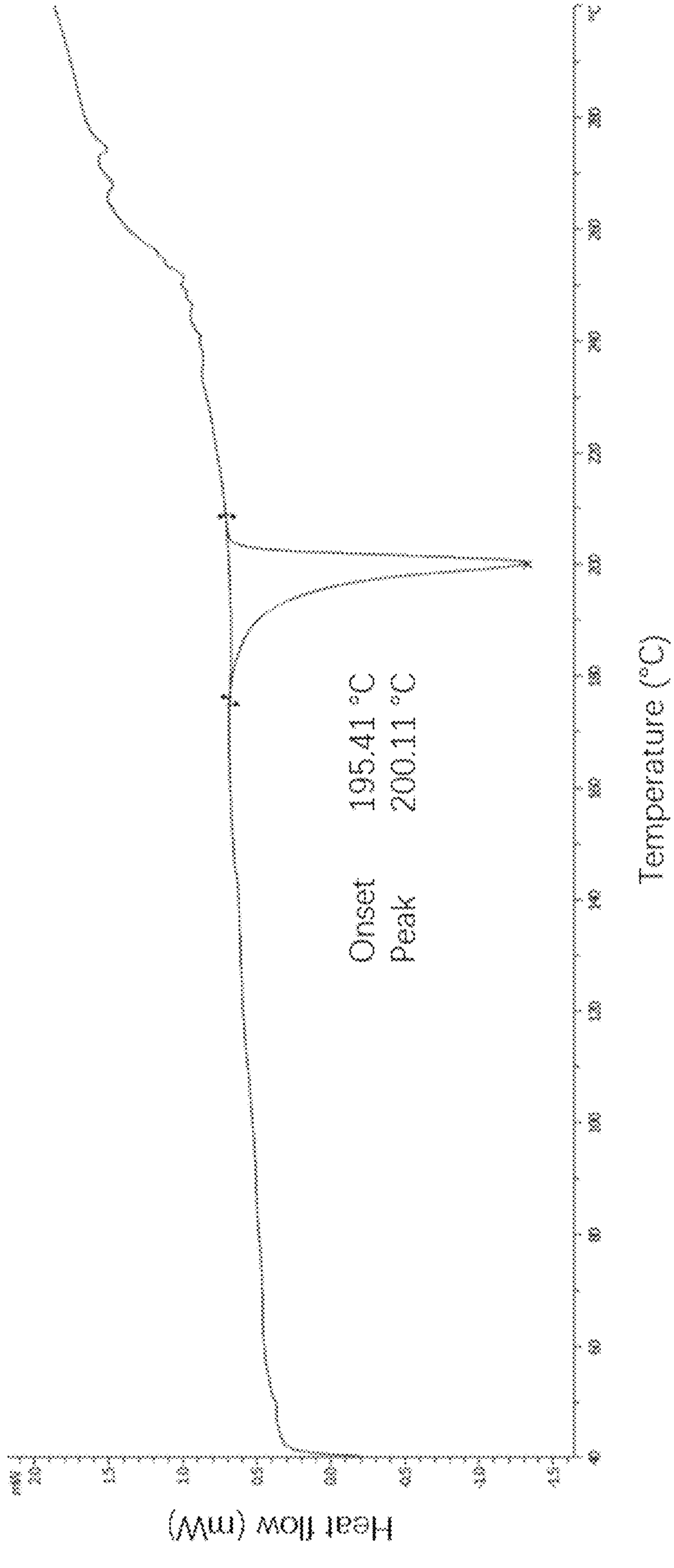
FIG. 3 shows the DSC spectrum of (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) hydrobromide (hydrobromide of Compound W) in the form of a crystal with crystal form I.

The result of differential scanning calorimetry (DSC) showed that the obtained solid showed an endothermic peak with an onset at 195.41° C. and a peak at 200.11° C., as shown in FIG. 3.

Figure 4:
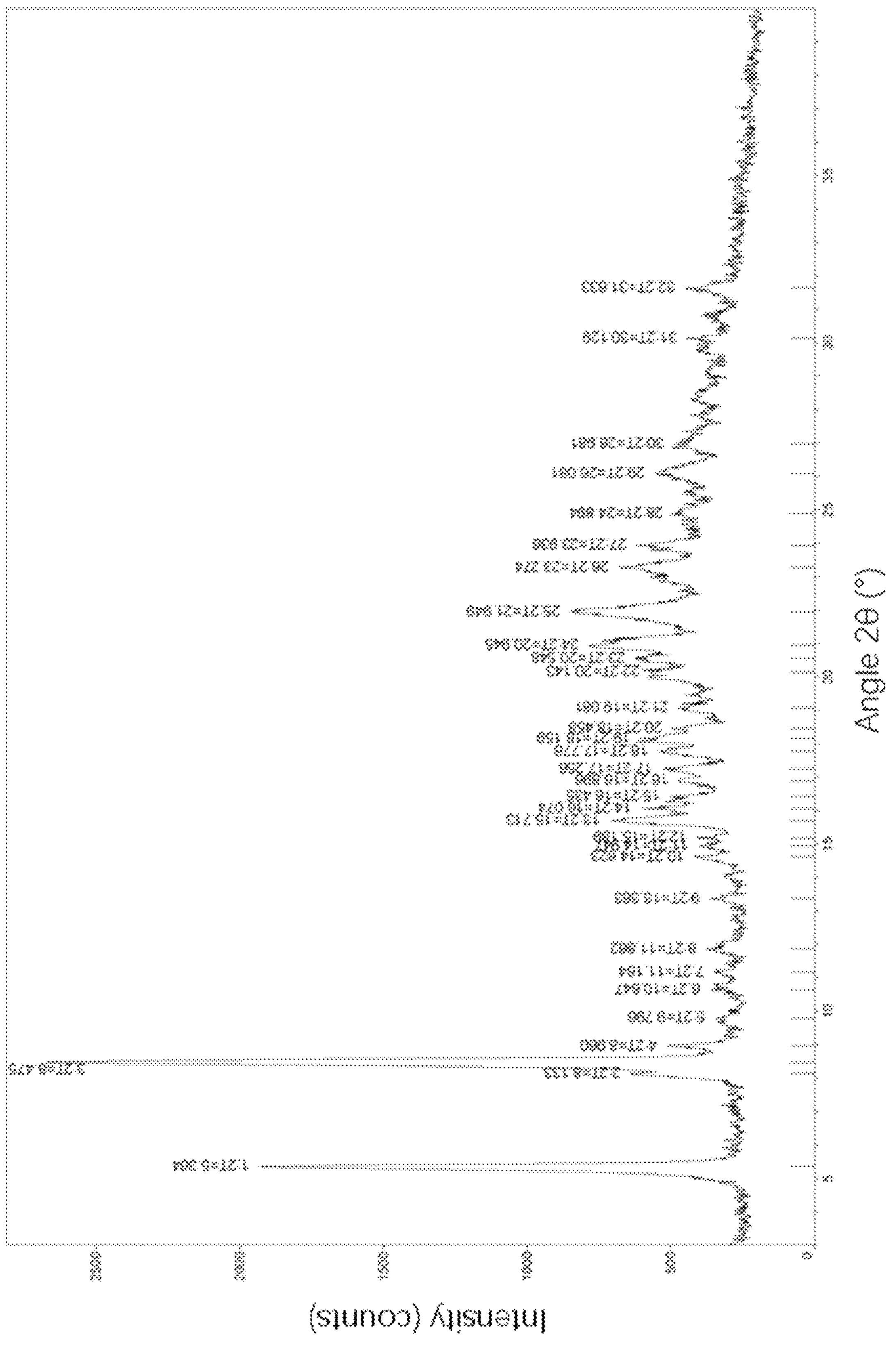
FIG. 4 shows the XRPD pattern of (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) hydrobromide (hydrobromide of Compound W) in the form of a crystal with crystal form I.

The results of X-ray powder diffraction (XRPD) showed that the obtained solid was in crystalline form, corresponding to crystal form I, as shown in Table 2 and FIG. 4.

TABLE 2

XRPD data for the hydrobromide of Compound W with crystal form I

| Peak number | Diffraction angle (2θ, °) | Intensity ($I/I_0$, %) |
|---|---|---|
| 1 | 5.364 | 61 |
| 2 | 8.133 | 26 |
| 3 | 8.475 | 100 |
| 4 | 8.960 | 7 |
| 5 | 9.796 | 3 |
| 6 | 10.647 | 6 |
| 7 | 11.164 | 6 |
| 8 | 11.862 | 4 |
| 9 | 13.363 | 2 |
| 10 | 14.623 | 2 |
| 11 | 14.947 | 5 |
| 12 | 15.189 | 5 |
| 13 | 15.713 | 17 |
| 14 | 16.074 | 18 |
| 15 | 16.435 | 8 |
| 16 | 16.896 | 7 |
| 17 | 17.256 | 9 |
| 18 | 17.776 | 9 |
| 19 | 18.159 | 19 |
| 20 | 18.458 | 11 |
| 21 | 19.081 | 3 |
| 22 | 20.143 | 5 |
| 23 | 20.548 | 11 |
| 24 | 20.945 | 20 |
| 25 | 21.949 | 24 |
| 26 | 23.274 | 15 |
| 27 | 23.936 | 5 |
| 28 | 24.894 | 5 |
| 29 | 26.081 | 13 |
| 30 | 26.981 | 8 |
| 31 | 30.129 | 6 |
| 32 | 31.633 | 5 |

Figure 7:
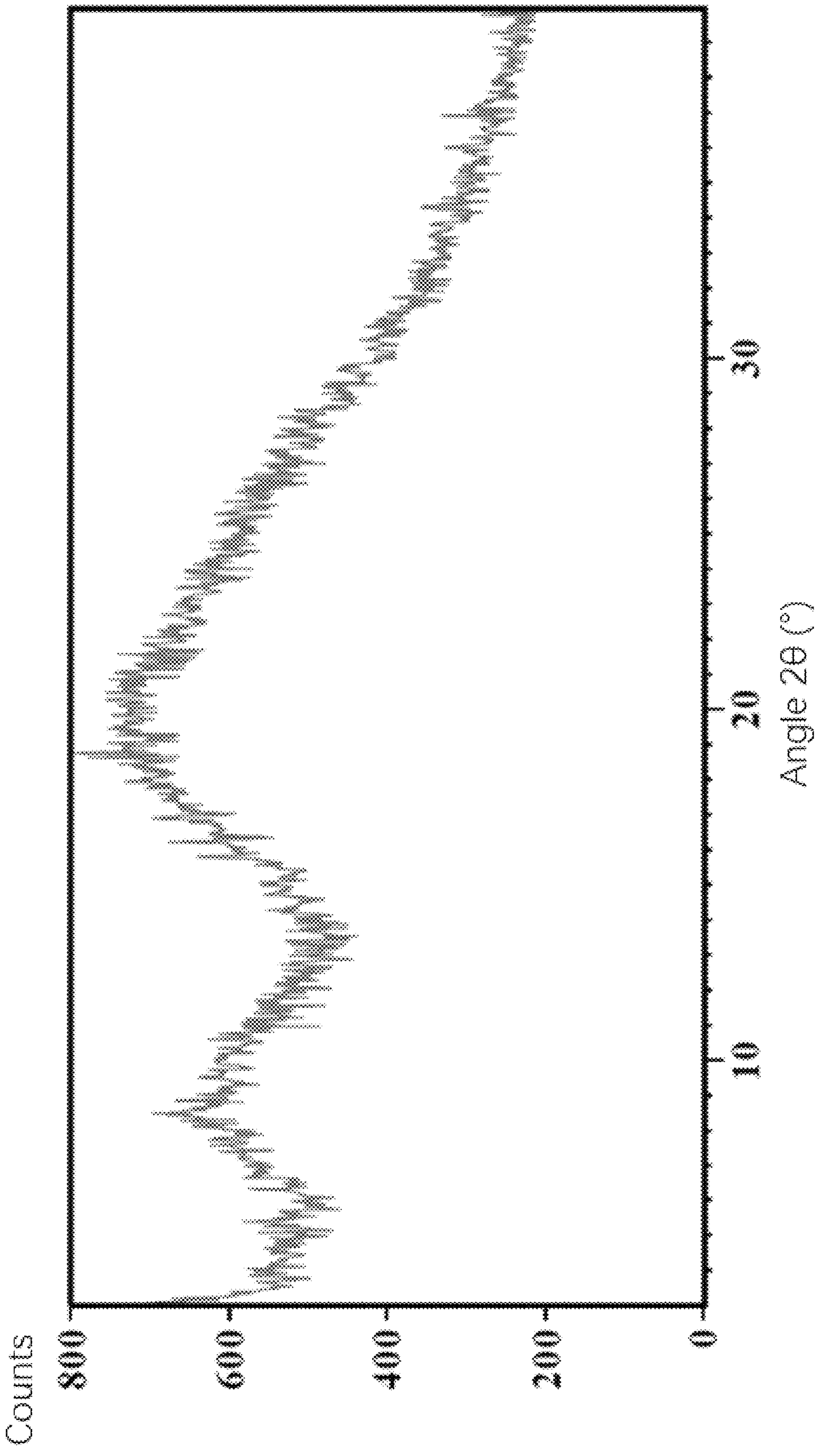
FIG. 7 shows the XRPD pattern of (2R,3R,4R,5R)-2-(4-aminopyrrolo[2,1-f][1,2,4]triazin-7-yl)-2-cyano-5-(isobutyryloxymethyl)tetrahydrofuran-3,4-diyl bis(2-methylpropanoate) hydrobromide (hydrobromide of Compound W) in amorphous form.

The solid powder (0.17 g) of the hydrobromide (I-2') of Compound W with crystal form I was added to ethanol (10 mL), stirred at room temperature. After the solid was completely dissolved, the solution was concentrated to remove the solvent, and drained by an oil pump, to obtain a powdered solid (0.17 g). The results of X-ray powder diffraction (XRPD) showed that the obtained solid was amorphous, as shown in FIG. 7.

Example 10: Performance Comparison Between Compound Z and its Acid Addition Salts 1) Comparison of Appearance and Preparation Between Compound Z and its Salts Compound Z and its different salts (prepared in Examples 1-8) were selected to compare the appearance and the difficulty level of preparation, as shown in Table 3.

TABLE 3

Appearance and preparation profile of Compound Z and its salts

| Compound | Appearance | Preparation |
|---|---|---|
| Compound Z | viscous oil | / |
| Hydrobromide of Compound Z | white powdery solid | The operation was simple, the solid was naturally precipitated, and easy to be filtered. |
| Hydrochloride of Compound Z | white powdery solid, only after grinding | The system was gelatinous, and it was difficult to be filtered. |
| Nitrate of Compound Z | white powdery solid | The operation was simple, the solid was naturally precipitated, and it was easy to be filtered. |
| Mesylate of Compound Z | white powdery solid | The solid was not prone to be naturally precipitated, and the filtration rate was slow. |
| Maleate of Compound Z | white powdery solid | The solid was not prone to be naturally precipitated, and the filtration rate was slow. |
| Hemisulfate of Compound Z | no solid | / |
| Sulfate of Compound Z | no solid | / |
| Phosphate of Compound Z | no solid | / |

As can be seen from the above table, except hemisulfate, sulfate and phosphate, the other acid addition salt forms of Compound Z had good appearance. In addition, the hydrobromide and nitrate salts of Compound Z are easier to be prepared.

2) Comparison of Hygroscopicity and Stability of Salts of Compound Z

Different salts of Compound Z (prepared in Examples 1-5) were selected to compare the hygroscopicity and stability, as shown in Table 4.

TABLE 4

Hygroscopicity and stability of salts of Compound Z

| Compound | Hygroscopicity | Stability |
|---|---|---|
| Hydrobromide of Compound Z | None, no increase in moisture content | Good stability under high temperature (80° C.), high humidity or light for 7 days |
| Hydrochloride of Compound Z | None, with an increase in moisture content of <0.1% | Good stability under high temperature (80° C.), high humidity or light for 7 days |
| Nitrate of Compound Z | None, with an increase in moisture content of <0.1% | Low melting point, at high temperature (80° C.), the solid melted, decomposed, and the color turned yellow. |
| Mesylate of Compound Z | None, with an increase in moisture content of <0.2% | In a high humidity environment, the solid decomposed obviously and had a peculiar smell. |
| Maleate of Compound Z | None, with an increase in moisture content of <0.1% | Good stability under high temperature (80° C.), high humidity or light for 7 days |

It can be seen from the above table that the hydrobromide, hydrochloride, nitrate, mesylate and maleate of Compound Z had no hygroscopicity at 25° C. and RH80%; the hydrobromide, hydrochloride and maleate of Compound Z were very stable under high temperature, light and high humidity conditions, while the stability of nitrate and mesylate of Compound Z was relatively poor.

3) Comparison of Solubility Between Compound Z and its Salts

Compound Z and its different salts (prepared in Examples 1, 4 and 5) were selected to compare their solubility.

An appropriate amount of sample was weighed and put in a glass test tube, to which a selected solvent was gradually added. The clarification process was observed. The solubility of various acid salts in deionized water was determined, as shown in Table 5.

TABLE 5

Solubility of Compound Z and its salts in deionized water

| Compound | Solubility in water (mg/mL) |
|---|---|
| Compound Z | 0.029 |
| Hydrobromide of Compound Z | 0.410 |
| Mesylate of Compound Z | 0.464 |
| Maleate of Compound Z | 0.351 |

It can be seen from the above table that the water solubility of Compound Z, as free base, was significantly lower than that of the salt of Compound Z, and the water solubility has a decisive influence on the preparation of pharmaceutical formulation, oral bioavailability, and the like. Therefore, the salification of Compound Z is more favorable for preparing a pharmaceutical formulation for human use.

Example 11: Performance Comparison Between Compound W and its Acid Addition Salts The steps of Example 10 were repeated, with the difference that Compound W and its different salts were taken to compare relative performances.

As in the case of Compound Z and its salts, the hydrobromide, hydrochloride, nitrate, mesylate, and maleate of Compound W were all white powdery solids, and the appearance of the above salts as solid material was significantly better than that of the free base. Among them, the hydrobromide, nitrate, mesylate and maleate of Compound W were easier to prepare, and the stability of hydrobromide and maleate was the best.

Example 12: Superiority of Hydrobromide of Compound Z with Crystal Form A

The hygroscopicity and stability of crystalline hydrobromide of Compound Z with crystal form A were investigated, as shown in Table 6.

TABLE 6

Hygroscopicity and stability of hydrobromide of Compound Z with crystal form A

| Item | Hydrobromide of Compound Z with crystal form A |
| --- | --- |
| Hygroscopicity | Placed for 24 hours under the conditions of 25° C., RH80%, with an increase in moisture content of <0.1%, no hygroscopicity |
| Stability | Good stability under high temperature (80° C.), high humidity or light conditions for 7 days<br>The crystal form was stable after being placed at 80° C. for 24 hours |

Figure 5:
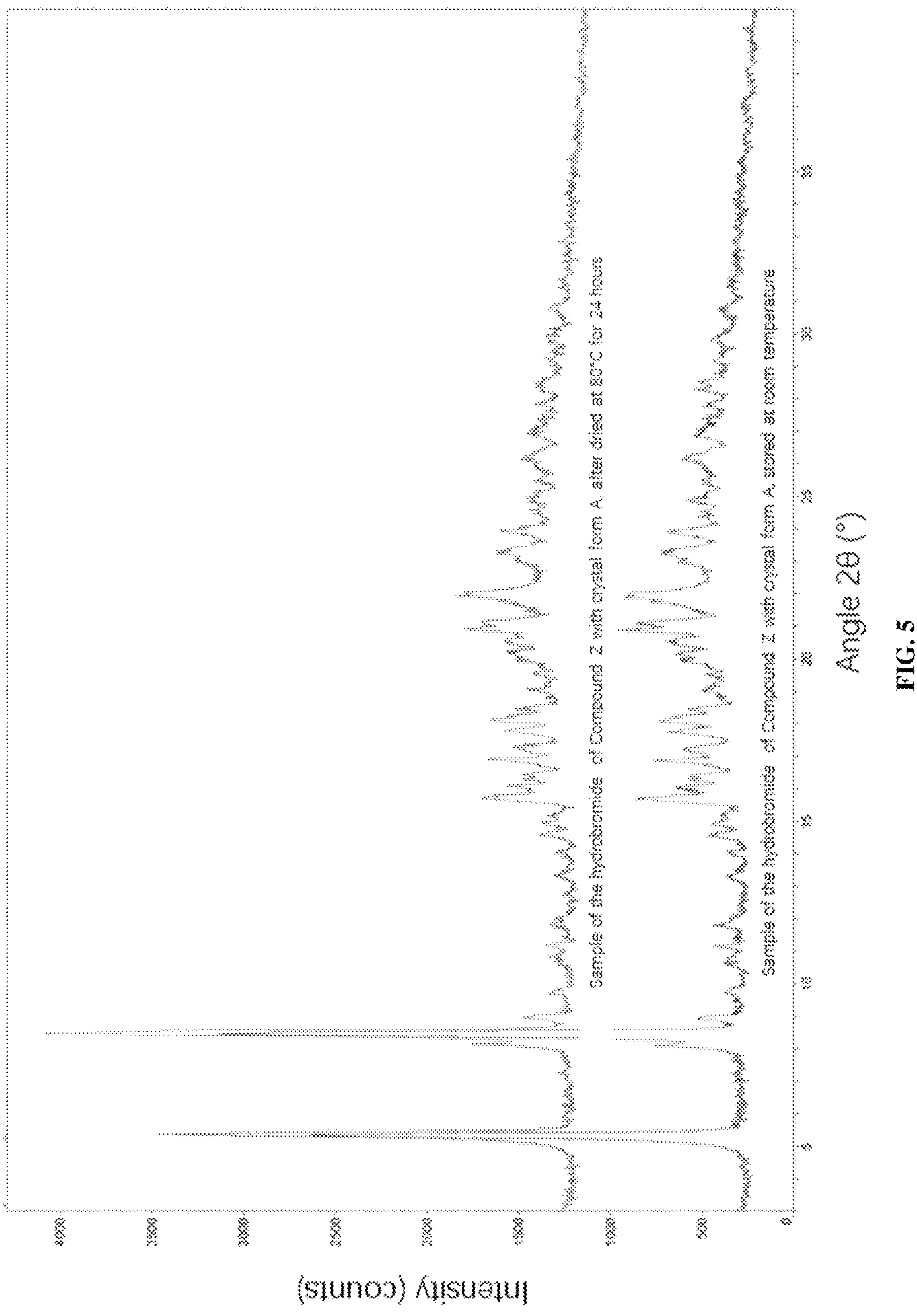
FIG. 5 shows an overlay of the XRPD patterns of (2R,3R,4R,5R)-2-(4-aminopyrrolo[2,1-f][1,2,4]triazin-7-yl-5-d)-2-cyano-5-(isobutyryloxymethyl)tetrahydrofuran-3,4-diyl bis(2-methylpropanoate) hydrobromide (hydrobromide of Compound Z) in the form of a crystal with crystal form A under different conditions (placed at room temperature and dried at 80° C. for 24 hours).

It can be seen from the above table that the hydrobromide of Compound Z with crystal form A had no hygroscopicity under high humidity conditions, and the crystal form was stable under high temperature (80° C.), as shown in FIG. 5.

Example 13: Superiority of Hydrobromide of Compound W with Crystal Form I

The hygroscopicity and stability of the crystalline hydrobromide of Compound W with crystal form I were investigated, as shown in Table 7.

TABLE 7

Hygroscopicity and stability of hydrobromide of Compound W with crystal form I

| Item | Hydrobromide of Compound W with crystal form I |
| --- | --- |
| Hygroscopicity | Placed for 24 hours under the conditions of 25° C., RH80%, with an increase in moisture content of <0.1%, no hygroscopicity |
| Stability | Good stability under high temperature (80° C.), high humidity or light conditions for 7 days |

It can be seen from the above table that the hydrobromide of Compound W with crystal form I had no hygroscopicity under high humidity conditions, and had good stability under high temperature (80° C.), high humidity or light conditions.

Example 14: Determination of the Component Ratio of the Hydrobromides of Compound Z and Compound W The component ratio of the hydrobromides of Compound Z and Compound W was determined by titration method.

For the hydrobromide of Compound Z prepared in Example 1 and the hydrobromide of Compound W prepared in Example 9, about 0.10 g of each sample was taken, accurately weighed, and dissolved in a mixed solution (20 mL) of equal volumes of methanol and water. The potentiometric titration was applied to determine the end point, and the titration was performed with a titration solution silver nitrate (0.1 mol/L), as shown in Table 8.

TABLE 8

Component ratio of the hydrobromides of Compound Z and Compound W

| Sample | Measured value of content of bromide ion (%) | Component ratio | Theoretical value of content of bromide ion (%) |
| --- | --- | --- | --- |
| Hydrobromide of Compound Z | 13.95 | 1:1 | 13.56 |
| Hydrobromide of Compound W | 13.96 | 1:1 | 13.58 |

It can be seen from the above table that Compound Z was salified with hydrogen bromide at a molar ratio of 1:1; Compound W was salified with hydrogen bromide at a molar ratio of 1:1.

Example 15: Pharmacokinetic Evaluation of the Hydrobromide of Compound Z in SD Rats Grouping: 30 SD rats were randomly divided into 5 groups, 6 rats in each group, half male and half female. Before administration, the rats were fasted for not less than 12 hours, and 4 hours after administration, they were fed uniformly.

Administration: the first group of animals received a single intravenous dose of 10 mg/kg of the hydrobromide of Compound Z in a solvent of DMSO/EtOH/PEG300/0.9% NaCl (5/5/40/50, v/v/v/v); the second to fourth groups of animals were given a single intragastric administration of 10 mg/kg, 30 mg/kg and 90 mg/kg of the hydrobromide of Compound Z, respectively, in a solvent of PEG400/Kolliphor® HS 15/ultrapure water (40/10/50, v/v/v); the fifth group of animals were given an intragastric administration of 30 mg/kg of the hydrobromide of Compound Z, once a day for 7 consecutive days.

Blood collection: before administration (0 h) and 5 min, 0.25, 0.5, 1, 2, 4, 6, 8, 10, 24, and 48 h after administration, 0.2 mL of blood was collected from the retroocular venous plexus or jugular vein (or by other methods of blood collection) from animals in each group, placed in an EDTA-K2 anticoagulation tube, and centrifuged at 2000 g for 10 minutes (4° C.) within 30 minutes, and the plasma was separated and stored at −70° C. for testing. The process from blood collection to centrifugation was performed under crushed ice conditions.

Data processing: LC-MS/MS technology was used to analyze the concentration of the nucleoside metabolite (2R,3R,4S,5R)-2-(4-aminopyrrolo[2,1-f][1,2,4]triazin-7-yl-5-d)-3,4-dihydroxy-5-(hydroxymethyl)tetrahydrofuran-2-carbonitrile in rat plasma, and to calculate pharmacokinetic parameters.

TABLE 9

Pharmacokinetic parameters of the nucleoside metabolite in plasma after intravenous administration in rats (n = 6, half male and half female)

| Gender | $AUC_{0-t}$ (ng · h/mL) | $AUC_{0-\infty}$ (ng · h/mL) | $MRT_{0-\infty}$ (h) | $t_{1/2}$ (h) | CL (mL/min/kg) | $V_{ss}$ (L/kg) |
|---|---|---|---|---|---|---|
| Male | 4446 ± 275 | 4473 ± 267 | 1.29 ± 0.08 | 1.11 ± 0.08 | 37.4 ± 2.3 | 2.89 ± 0.03 |
| Female | 4718 ± 69 | 4760 ± 68 | 1.35 ± 0.10 | 1.77 ± 0.60 | 35.0 ± 0.5 | 2.84 ± 0.25 |
| Total | 4582 ± 233 | 4616 ± 235 | 1.32 ± 0.09 | 1.44 ± 0.53 | 36.2 ± 2.0 | 2.87 ± 0.16 |

TABLE 10

Pharmacokinetic parameters of the nucleoside metabolite in plasma after intragastric administration in rats (n = 6, half male and half female)

| Dose (mg/kg) | Gender | $T_{max}$ (h) | $C_{max}$ (ng/mL) | $AUC_{0-t}$ (ng · h/mL) | $AUC_{0-\infty}$ (ng · h/mL) | $t_{1/2}$ (h) | F % |
|---|---|---|---|---|---|---|---|
| 10 | male | 1.0 | 608 ± 92 | 3322 ± 162 | 3403 ± 142 | 1.51 ± 0.29 | |
| | female | 1.0 | 963 ± 136 | 4598 ± 428 | 4689 ± 504 | 1.36 ± 0.28 | |
| | total | 1.0 | 785 ± 220 | 3960 ± 757 | 4046 ± 778 | 1.43 ± 0.27 | 86.4% |
| 30 | male | 1.0 | 1563 ± 340 | 8652 ± 423 | 9575 ± 312 | 2.85 ± 0.78 | |
| | female | 0.5 | 2573 ± 83 | 13114 ± 244 | 13342 ± 220 | 1.33 ± 0.15 | |
| | total | 0.75 | 2068 ± 596 | 10883 ± 2463 | 11458 ± 2077 | 2.09 ± 0.98 | 79.2% |
| 90 | male | 0.5 | 5107 ± 1347 | 33181 ± 3573 | 33237 ± 3572 | 3.32 ± 1.41 | |
| | female | 2.0 | 6973 ± 1221 | 32433 ± 1162 | 32533 ± 1221 | 3.96 ± 1.86 | |
| | total | 0.75 | 6040 ± 1539 | 32807 ± 2412 | 32885 ± 2418 | 3.64 ± 1.52 | 79.6% |
| 7 × 30 | male | 2.0 | 1913 ± 210 | 7917 ± 1082 | 9519 ± 1372 | 4.15 ± 3.95 | |
| | female | 2.0 | 1567 ± 145 | 7569 ± 872 | 9083 ± 1392 | 3.68 ± 0.94 | |
| | total | 2.0 | 1740 ± 249 | 7743 ± 899 | 9301 ± 1259 | 3.92 ± 2.58 | |

It can be seen from Table 9 that after intravenous administration (10 mg/kg) of the hydrobromide of Compound Z to SD rats, the nucleoside metabolite was rapidly eliminated in plasma, with an average half-life ($t_{1/2}$) of 1.44±0.53 h.

It can be seen from Table 10 that after intragastric administration to SD rats, the hydrobromide of Compound Z was rapidly absorbed, and rapidly transformed into the nucleoside metabolite, and maximum blood drug concentration ($C_{max}$) was reached in about 1 hour. After a single intragastric administration of 10, 30 and 90 mg/kg, the bioavailability (F %) of the hydrobromide of Compound Z, calculated based on the nucleoside metabolite, was 86.4%, 79.2% and 79.6%, respectively. After multiple intragastric administration (30 mg/kg, once a day for 7 consecutive days), the $C_{max}$ and $AUC_{0-t}$ of the nucleoside metabolite in plasma on the $7^{th}$ day were 0.84 and 0.71 times of those after a single administration, respectively, indicating that there was no accumulation of nucleoside metabolite in rats.

Example 16: Pharmacokinetic Evaluation of the Hydrobromide of Compound Z in Beagle Dogs Grouping: 18 beagle dogs were randomly divided into 3 groups (A, B and C), 6 dogs in each group, half male and half female. Before administration, the dogs were fasted for not less than 12 hours, and 4 hours after administration, they were fed uniformly.

Administration: The administration was performed in two periods, with a one-week washout period. In the first period, the animals in groups A and B were given a single intragastric administration of 10 mg/kg and 20 mg/kg of the hydrobromide of Compound Z, respectively; the animals in group C were given an intragastric administration of 20 mg/kg of the hydrobromide of Compound Z, once a day for 7 consecutive days, in a solvent of PEG400/Kolliphor® HS 15/ultrapure water (40/10/50, v/v/v). In the second period, the animals in groups A and B were given a single intravenous and intragastric administration of 10 mg/kg and 40 mg/kg of the hydrobromide of Compound Z, respectively; the solvent for intravenous administration was DMSO/EtOH/PEG300/0.9% NaCl (5/5/40/50, v/v/v/v), and the solvent for intragastric administration was the same as that in the first period.

Blood collection: Before administration (0 h) and 5 min (intravenous injection group only), 0.25, 0.5, 1, 2, 4, 6, 8, 10, 24, and 48 h after administration, 1.0 mL of blood was collected from the forelimb vein or other parts of the animals in each group, placed in an anticoagulant blood collection tube containing a stabilizer. After processing, the plasma was separated and stored in a −70° C. freezer.

Data processing: LC-MS/MS technology was used to analyze the concentration of the nucleoside metabolite (2R,3R,4S,5R)-2-(4-aminopyrrolo[2,1-f][1,2,4]triazin-7-yl-5-d)-3,4-dihydroxy-5-(hydroxymethyl)tetrahydrofuran-2-carbonitrile in beagle dog plasma, and to calculate pharmacokinetic parameters.

TABLE 11

| Pharmacokinetic parameters of the nucleoside metabolite in plasma after intravenous administration in beagle dogs (n = 6, half male and half female) | | | | | | |
|---|---|---|---|---|---|---|
| Gender | $AUC_{0-t}$ (ng · h/mL) | $AUC_{0-\infty}$ (ng · h/mL) | $MRT_{0-\infty}$ (h) | $t_{1/2}$ (h) | CL (mL/min/kg) | $V_{ss}$ (L/kg) |
| Male | 14697 ± 3569 | 14934 ± 3451 | 3.60 ± 0.75 | 3.54 ± 1.09 | 11.6 ± 2.8 | 2.42 ± 0.06 |
| Female | 16973 ± 2150 | 17168 ± 2187 | 4.10 ± 0.33 | 4.34 ± 0.37 | 9.82 ± 1.34 | 2.41 ± 0.20 |
| Total | 15835 ± 2916 | 16051 ± 2859 | 3.85 ± 0.58 | 3.94 ± 0.85 | 10.7 ± 2.2 | 2.41 ± 0.13 |

TABLE 12

| Pharmacokinetic parameters of the nucleoside metabolite in plasma after intragastric administration in beagle dogs (n = 6, half male and half female) | | | | | | | |
|---|---|---|---|---|---|---|---|
| Dose (mg/kg) | Gender | $T_{max}$ (h) | $C_{max}$ (ng/mL) | $AUC_{0-t}$ (ng · h/mL) | $AUC_{0-\infty}$ (ng · h/mL) | $t_{1/2}$ (h) | F % |
| 10 | male | 1.17 ± 0.76 | 3407 ± 404 | 13801 ± 3550 | 14015 ± 3503 | 4.98 ± 1.33 | |
| | female | 0.83 ± 0.29 | 3030 ± 960 | 13889 ± 2895 | 14312 ± 2939 | 4.07 ± 1.86 | |
| | total | 1.00 ± 0.55 | 3218 ± 690 | 13845 ± 2898 | 14163 ± 2896 | 4.53 ± 1.53 | 87.4% |
| 20 | male | 0.83 ± 0.29 | 7143 ± 301 | 30010 ± 3992 | 30365 ± 4085 | 4.16 ± 0.25 | |
| | female | 1.33 ± 0.58 | 6123 ± 2208 | 34401 ± 4003 | 34968 ± 4094 | 4.25 ± 1.13 | |
| | total | 1.08 ± 0.49 | 6633 ± 1516 | 32206 ± 4309 | 32667 ± 4442 | 4.21 ± 0.73 | 101.7% |
| 40 | male | 0.83 ± 0.29 | 11693 ± 5519 | 56111 ± 13640 | 56754 ± 13685 | 4.02 ± 0.46 | |
| | female | 1.33 ± 0.58 | 10423 ± 3978 | 70468 ± 5504 | 71115 ± 5753 | 4.52 ± 0.88 | |
| | total | 1.08 ± 0.49 | 11058 ± 4359 | 63289 ± 12181 | 63935 ± 12248 | 4.27 ± 0.68 | 99.9% |
| 7 × 20 | male | 1.33 ± 0.58 | 5727 ± 2138 | 26956 ± 4076 | 27258 ± 4196 | 4.03 ± 0.24 | |
| | female | 1.00 ± 0.87 | 6907 ± 3478 | 27788 ± 3360 | 28268 ± 3411 | 4.65 ± 0.27 | |
| | total | 1.17 ± 0.68 | 6317 ± 2662 | 27372 ± 3372 | 27763 ± 3464 | 4.34 ± 0.41 | |

It can be seen from Table 11 that after intravenous administration (10 mg/kg) of the hydrobromide of Compound Z to beagle dogs, an average $t_{1/2}$ of the nucleoside metabolite was 3.94±0.85 h.

It can be seen from Table 12 that after intragastric administration to beagle dogs, the hydrobromide of Compound Z was rapidly absorbed, and rapidly transformed into the nucleoside metabolite, $C_{max}$ was reached in about 1 hour, and $t_{1/2}$ was 4.21 h at a dose of 20 mg/kg. After a single intragastric administration of 10, 20 and 40 mg/kg, the F % of the hydrobromide of Compound Z, calculated based on the nucleoside metabolite, was 87.4%, 101.7% and 99.9%, respectively. After multiple intragastric administration (20 mg/kg, once a day for 7 consecutive days), the $C_{max}$ and $AUC_{0-t}$ of the nucleoside metabolite in plasma on the $7^{th}$ day were 0.95 and 0.85 times of those after a single administration, respectively, indicating that there was no accumulation of nucleoside metabolite in beagle dogs.

Example 17: In Vivo Safety Evaluation of the Hydrobromide of Compound Z in SD Rats and Beagle Dogs The safety of the hydrobromide of Compound Z in SD rats and beagle dogs was evaluated in accordance with the "Good Laboratory Practice" (2017) issued by the National Medical Products Administration (NMPA), and the acute toxicity test and 14-day long-term toxicity test were carried out, respectively.

1. Toxicity Test of a Single Intragastric Administration to SD Rats

Method: 40 SD rats were randomly divided into 4 groups, 10 rats in each group, half male and half female. The rats were given a single intragastric administration of a solvent of PEG400/Kolliphor® HS 15/ultrapure water (40/10/50, v/v/v) and the hydrobromide of Compound Z (200, 600 and 2000 mg/kg, based on the free base) dissolved in this solvent, respectively. After administration, observation was continued for 14 days, and dissection was performed on the 15th day as planned. During the test, clinical observations, body weight, feed consumption and anatomical and morphological observations by naked eyes were evaluated.

Results: during the test, there was no early death or euthanasia of animals in each group; no abnormal clinical symptoms were found in the animals of each dose group during the test; compared with the control group, the average body weight and feed consumption of the animals in each administration group had no changes related to the test article; there was no abnormality in the anatomical observation by naked eyes.

In summary, under the conditions of this test, when SD rats were given a single intragastric administration of 200, 600 or 2000 mg/kg of the hydrobromide of Compound Z, the test article was well tolerated in all animals, and the maximum tolerated dose (MTD) was greater than or equal to 2000 mg/kg.

2. Toxicity Test of a Single Intragastric Administration to Beagle Dogs

Method: 8 beagle dogs were randomly divided into 4 groups, 2 dogs in each group, one male and one female. The dogs were given a single intragastric administration of a solvent of PEG400/Kolliphor® HS 15/ultrapure water (40/10/50, v/v/v) and the hydrobromide of Compound Z (50, 250 and 1000 mg/kg, based on the free base) dissolved in this solvent, respectively. After administration, observation was continued for 14 days, and dissection was performed on the 15th day as planned. Clinical observations, body weight, feed consumption, clinical pathology (blood, blood coagulation, plasma biochemistry), and morphological observation by naked eyes were evaluated.

Results: during the test, no accidental death occurred in each group of animals; in the 1000 mg/kg dose group, vomit containing suspicious drug was observed only in female animal on day 1, while soft stools and vomit containing feed were observed in male animal on day 2; in the 1000 mg/kg dose group, only the male animal showed a significant decrease in body weight on day 2; compared with the control group, no obvious changes related to the test article were observed in the feed consumption, clinical pathology and anatomical observation by naked eyes of the animals in each administration group.

In summary, under the conditions of this test, when beagle dogs were given a single intragastric administration of 50, 250 or 1000 mg/kg of the hydrobromide of Compound Z, the test article was well tolerated in all animals, and the maximum tolerated dose (MTD) was greater than or equal to 1000 mg/kg.

3. Toxicity Test of SD Rats by Continuous Gavage for 14 Days and Drug Withdrawal for 14 Days Method: 120 SD rats were randomly divided into 4 groups, 30 rats in each group, half male and half female. The rats were given an intragastric administration of a solvent of PEG400/Kolliphor® HS15/ultrapure water (40/10/50, v/v/v) and the hydrobromide (100, 300 and 600 mg/kg) of Compound Z dissolved in the solvent, respectively, once a day for 14 consecutive days; two-thirds of the animals in each group (20 animals in each group, half male and half female) were dissected after the end of the administration period (day 15); the remaining animals in each group (10 animals in each group, half male and half female) were dissected at the end of the 14-day recovery period (day 29). The following indexes were observed, measured and evaluated: clinical observations, body weight, feed consumption, ophthalmological examination, hematology, blood coagulation, plasma biochemistry and plasma electrolytes, urinalysis, anatomical and morphological observation by naked eyes, organ weight and histopathological examination, and the accompanying rat bone marrow micronucleus test.

Results: during the test, two animals in the 600 mg/kg dose group died, and it was uncertain that the cause of death was drug-related. In the dose groups of 300 mg/kg and 600 mg/kg, adverse drug reactions in hematology, plasma biochemistry, urinalysis, pathological examination, and the like could be observed in the animals. At the end of the recovery period, the various indexes returned to normal or showed a recovery trend.

In summary, under the conditions of this test, SD rats were given an intragastric administration of 100, 300 or 600 mg/kg of the hydrobromide of Compound Z once a day for 14 consecutive days, followed by drug withdrawal and recovery for 14 days, and the no-observed-adverse-effect level (NOAEL) in males and females was 100 mg/kg.

4. Toxicity Test of Beagle Dogs by Intragastric Administration for 14 Days and Drug Withdrawal for 14 Days Test method: 40 beagle dogs were randomly divided into 4 groups, 10 dogs in each group, half male and half female. The dogs were given an intragastric administration of a solvent of PEG400/Kolliphor® HS15/ultrapure water (40/10/50, v/v/v) and the hydrobromide (30, 100 and 250 mg/kg) of Compound Z dissolved in the solvent, respectively, once a day for 14 consecutive days; three-fifths of the animals in each group (6 animals in each group, half male and half female) were dissected after the end of the administration period (day 15); the remaining animals in each group (4 animals in each group, half male and half female) were dissected at the end of the 14-day recovery period (day 29). The following indexes were observed, measured and evaluated: clinical observations, ophthalmological examination, body weight, feed consumption, body temperature, electrocardiogram (HR, PR interval, QRS interval, T wave amplitude, QT interval and QTcV interval), clinical Pathology (hematology, blood coagulation, plasma biochemistry, urine), pathological examination (morphological observation by naked eyes, organ weight, histopathological examination).

Results: during the test, no accidental death occurred in each group of animals. In the dose groups of 250 mg/kg and 100 mg/kg, adverse drug reactions in ophthalmological examination, clinical pathology, pathological examination, and the like could be observed in the animals. At the end of the recovery period, the various indexes returned to normal or showed a recovery trend.

In summary, under the conditions of this test, beagle dogs were given an intragastric administration of 30, 100 or 250 mg/kg of the hydrobromide of Compound Z once a day for 14 consecutive days, followed by drug withdrawal and recovery for 14 days, and the no-observed-adverse-effect level (NOAEL) in males and females was 30 mg/kg.

All documents mentioned herein are incorporated by reference in the present application as if each of them is individually incorporated by reference. Besides, it should be understood that those skilled in the art can make various adjustments or modifications to the present disclosure after reading the above content thereof, and these equivalent forms also fall within the scope defined by the appended claims of the present application.

The invention claimed is:

1. A crystal form of a compound of formula I-1';

I-1'

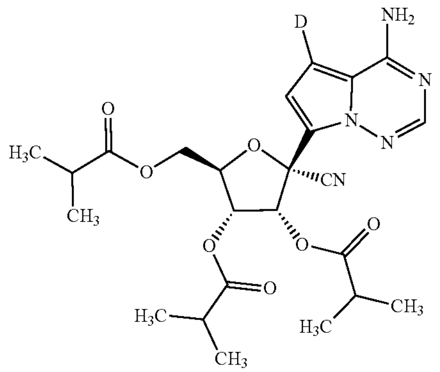

•HBr.

wherein the crystal form is a crystal form A, and wherein the crystal form A has at least one of the following characteristics:

1) an XRPD pattern of the crystal form A at least having characteristic peaks at 3-7 positions among the following 2θ values of 5.35°±0.2°, 8.11°±0.2°, 8.46°±0.2°, 15.70°±0.2°, 18.08°±0.2°, 21.09°±0.2° and 21.91°±0.2°; or the XRPD pattern of the crystal form A further at least has characteristic peaks at 3-8 positions among the following 2θ values of 16.02°±0.2°, 16.88°±0.2°, 17.22°±0.2°, 17.76°±0.2°, 20.55°±0.2°, 23.25°±0.2°, 23.89°±0.2° and 26.14°±0.20; or the XRPD pattern of the crystal form A is shown in FIG. 2;

2) a DSC spectrum of the crystal form A having an absorption peak at 204±5° C.; or the DSC spectrum of the crystal form A is shown in FIG. 1;

3) after being placed under conditions of 25° C. and RH80% for 24 hours, the crystal form A showing an increase in moisture content of 1% or less; and 4) at 37° C., the crystal form A having a solubility in deionized water of 0.1 mg/mL or more.

2. A crystal form of a compound of formula I-2';

I-2'

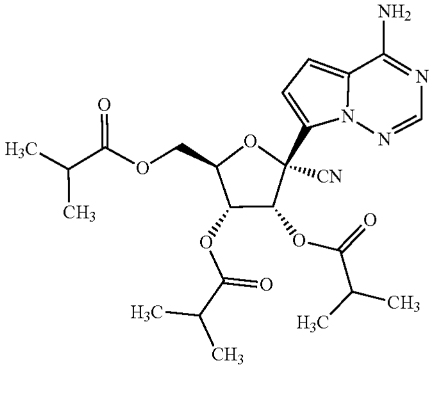

•HBr.

wherein the crystal form is a crystal form I, and wherein the crystal form I has at least one of the following characteristics:

1) an XRPD pattern of the crystal form I at least having characteristic peaks at 3-6 positions among the following 2θ values of 5.36°±0.2°, 8.13°±0.2°, 8.48°±0.2°, 18.16°±0.2°, 20.95°±0.2° and 21.95°±0.2°; or the XRPD pattern of the crystal form I further at least has characteristic peaks at 3-7 positions among the following 2θ values of 15.71°±0.2°, 16.07°±0.2°, 16.90°±0.2°, 17.26°±0.2°, 20.55°±0.2°, 23.27°±0.2° and 26.08°±0.2°; or the XRPD pattern of the crystal form I is shown in FIG. 4;

2) a DSC spectrum of the crystal form I having an absorption peak at 200±5° C.; or the DSC spectrum of the crystal form I is shown in FIG. 3;

3) after being placed under conditions of 25° C. and RH80% for 24 hours, the crystal form I showing an increase in moisture content of 1% or less; and 4) at 37° C., the crystal form I having a solubility in deionized water of 0.1 mg/mL or more.

3. A preparation method of the crystal form according to claim 1, comprising the following steps of 1) dissolving a compound of formula II in a solvent A to obtain a solution A, and mixing the solution A with an acid or a solution B obtained by dissolving the acid in a solvent B under an ice bath condition to obtain a mixed solution;

II

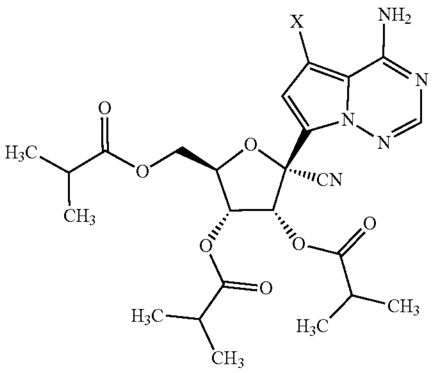

wherein

X is deuterium;

the acid is hydrogen bromide;

2) stirring and concentrating the mixed solution at room temperature to obtain a target product, and 3) mixing the product in step 2) with a solvent C, stirring at room temperature and/or under a heating condition to precipitate a solid as a target product.

4. The preparation method according to claim 3, wherein in step 1), the solvent A is acetonitrile; a dosage ratio of the compound of formula II and the acetonitrile is 1 g: 2 to 20 mL; the solvent B is water, the solution B is hydrobromic acid, and a content of hydrogen bromide in the hydrobromic acid is 40 wt % to 50 wt %; a molar ratio of the compound of formula II to the hydrogen bromide is 1:0.9 to 1;

in step 2), the stirring lasts for 0.5 to 5 hours;

in step 3), the solvent C is methyl tert-butyl ether; a dosage ratio of the compound of formula II and the methyl tert-butyl ether is 1 g: 2 to 20 mL; the heating condition is heating at a temperature ranging from 35 to 60° C.; and the stirring lasts for 0.5 to 5 hours.

5. A pharmaceutical composition, comprising 1) the crystal form according to claim 1; and 2) an optional pharmaceutically acceptable excipient;

or the pharmaceutical composition is an oral formulation or a non-oral formulation;

the oral formulation is selected from the group consisting of tablet, capsule, granule, powder and syrup;

the non-oral formulation is selected from the group consisting of injection, powder for injection, spray and suppository.

6. A method for treating and/or alleviating a disease caused by a coronavirus, comprising a step of administering a therapeutically and/or palliatively effective amount of the crystal form according to claim 1 to a subject in need thereof.

7. A method for inhibiting replication of a coronavirus, comprising a step of contacting the coronavirus, with an inhibitory effective amount of the crystal form according to claim 1.

8. A method for treating and/or alleviating a disease caused by a coronavirus, comprising a step of administering a therapeutically and/or palliatively effective amount of the pharmaceutical composition according to claim 5 to a subject in need thereof.

9. A method for inhibiting replication of a coronavirus, comprising a step of contacting the coronavirus, with an inhibitory effective amount of the pharmaceutical composition according to claim 5.

10. A preparation method of the crystal form according to claim 2, comprising the following steps of 1) dissolving a compound of formula II in a solvent A to obtain a solution A, and mixing the solution A with an acid or a solution B obtained by dissolving the acid in a solvent B under an ice bath condition to obtain a mixed solution;

II

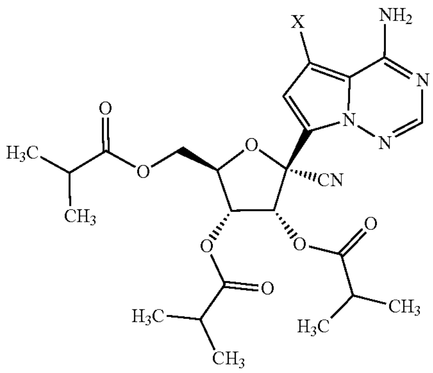

wherein

X is hydrogen;

the acid is hydrogen bromide;

2) stirring and concentrating the mixed solution at room temperature to obtain a target product; and 3) mixing the product in step 2) with a solvent C, stirring at room temperature and/or under a heating condition to precipitate a solid as a target product.

11. The preparation method according to claim 10, wherein in step 1), the solvent A is acetonitrile; a dosage ratio of the compound of formula II and the acetonitrile is 1 g: 2 to 20 mL; the solvent B is water, the solution B is hydrobromic acid, and a content of hydrogen bromide in the hydrobromic acid is 40 wt % to 50 wt %; a molar ratio of the compound of formula II to the hydrogen bromide is 1:0.9 to 1;

in step 2), the stirring lasts for 0.5 to 5 hours;

in step 3), the solvent C is methyl tert-butyl ether; a dosage ratio of the compound of formula II and the methyl tert-butyl ether is 1 g:2 to 20 mL; the heating condition is heating at a temperature ranging from 35 to 60° C.; and the stirring lasts for 0.5 to 5 hours.

12. A pharmaceutical composition, comprising 1) the crystal form according to claim 2; and 2) an optional pharmaceutically acceptable excipient;

or the pharmaceutical composition is an oral formulation or a non-oral formulation;

the oral formulation is selected from the group consisting of tablet, capsule, granule, powder and syrup;

the non-oral formulation is selected from the group consisting of injection, powder for injection, spray and suppository.

13. A method for treating and/or alleviating a disease caused by a coronavirus, comprising a step of administering a therapeutically and/or palliatively effective amount of the crystal form according to claim 2 to a subject in need thereof.

14. A method for inhibiting replication of a coronavirus, comprising a step of contacting the coronavirus, with an inhibitory effective amount of the crystal form according to claim 2.

15. A method for treating and/or alleviating a disease caused by a coronavirus, comprising a step of administering a therapeutically and/or palliatively effective amount of the pharmaceutical composition according to claim 12 to a subject in need thereof.

16. A method for inhibiting replication of a coronavirus, comprising a step of contacting the coronavirus, with an inhibitory effective amount of the pharmaceutical composition according to claim 12.

* * * * *